(12) United States Patent
Funk et al.

(10) Patent No.: US 11,975,159 B2
(45) Date of Patent: May 7, 2024

(54) STABILIZATION DEVICES FOR VASCULAR ACCESS AND METHODS OF USING THE SAME

(71) Applicant: Velano Vascular, Inc., San Francisco, CA (US)

(72) Inventors: Brian J. Funk, San Francisco, CA (US); Pitamber Devgon, Philadelphia, PA (US)

(73) Assignee: Velano Vascular, Inc., San Francisco, CA (US)

( * ) Notice: Subject to any disclaimer, the term of this patent is extended or adjusted under 35 U.S.C. 154(b) by 0 days.

(21) Appl. No.: 17/528,993

(22) Filed: Nov. 17, 2021

(65) Prior Publication Data
US 2022/0072278 A1    Mar. 10, 2022

Related U.S. Application Data

(62) Division of application No. 15/992,661, filed on May 30, 2018, now Pat. No. 11,207,501.
(Continued)

(51) Int. Cl.
*A61M 25/02*    (2006.01)
*A61M 25/00*    (2006.01)

(52) U.S. Cl.
CPC ........ *A61M 25/02* (2013.01); *A61M 25/0097* (2013.01); *A61M 25/0017* (2013.01);
(Continued)

(58) Field of Classification Search
CPC .............. A61M 25/02; A61M 25/0097; A61M 25/0017; A61M 2025/0253; A61M 2025/028
(Continued)

(56) References Cited

U.S. PATENT DOCUMENTS 4,468,224 A    8/1984 Enzmann et al.
4,517,971 A    5/1985 Sorbonne
(Continued)

FOREIGN PATENT DOCUMENTS

CA    2678253 A1    11/1999
CN    104302346 A    1/2015
(Continued)

OTHER PUBLICATIONS

Velano Vascular, "Introducing PIVO" [Retrieved from the Internet] <URL:http://velanovascular.com/solutions/>, 2017.

*Primary Examiner* — Phillip A Gray
(74) *Attorney, Agent, or Firm* — The Webb Law Firm

(57) ABSTRACT

A stabilization device configured to stabilize an access device when a distal end portion of the access device is inserted through a target location of a patient. The stabilization device includes a coupling surface, a proximal surface, and a base surface. The coupling surface is configured to be placed in contact with an adapter coupled to a proximal end portion of the access device. The proximal surface forms at least one angle and is configured to facilitate securement of the stabilization device to the target location. The base surface forms a contoured portion configured to be placed in contact with the target location and a recessed portion configured to be spaced apart from the target location. The stabilization device is configured to be secured to the target location such that the adapter is retained in a fixed position relative to the coupling surface and the access device is stabilized.

7 Claims, 9 Drawing Sheets

Related U.S. Application Data

(60) Provisional application No. 62/512,332, filed on May 30, 2017.

(52) U.S. Cl.
CPC .............. *A61M 2025/0253* (2013.01); *A61M 2025/028* (2013.01)

(58) Field of Classification Search
USPC ........................................................ 604/174
See application file for complete search history.

(56) References Cited

U.S. PATENT DOCUMENTS

| | | | |
|---|---|---|---|
| 4,578,063 A | 3/1986 | Innman et al. | |
| 5,336,195 A | 8/1994 | Daneshvar | |
| 5,556,381 A | 9/1996 | Ensiminger et al. | |
| 5,681,290 A | 10/1997 | Alexander | |
| 5,693,032 A | 12/1997 | Bierman | |
| 5,755,225 A | 5/1998 | Hutson | |
| 5,807,342 A | 9/1998 | Musgrave et al. | |
| 5,810,781 A | 9/1998 | Bierman et al. | |
| 5,833,666 A | 11/1998 | Davis et al. | |
| 6,086,564 A | 7/2000 | McLaughlin | |
| 6,213,979 B1 | 4/2001 | Bierman | |
| 6,283,945 B1 | 9/2001 | Bierman | |
| 6,332,874 B1 | 12/2001 | Eliasen et al. | |
| 6,361,523 B1 | 3/2002 | Bierman | |
| 6,413,240 B1 | 7/2002 | Bierman et al. | |
| 6,418,966 B2 | 7/2002 | Loo | |
| 6,428,513 B1 | 8/2002 | Abrahamson | |
| 6,551,284 B1 | 4/2003 | Greenberg et al. | |
| 6,663,600 B2 | 12/2003 | Bierman et al. | |
| 6,929,625 B2 | 8/2005 | Bierman | |
| 6,951,550 B2 | 10/2005 | Bierman | |
| 7,014,627 B2 | 3/2006 | Bierman | |
| 7,018,362 B2 | 3/2006 | Bierman et al. | |
| 7,198,616 B2 | 4/2007 | Mossanen-Shams et al. | |
| 7,223,256 B2 | 5/2007 | Bierman | |
| 7,247,150 B2 | 7/2007 | Bierman | |
| 7,563,251 B2 | 7/2009 | Bierman et al. | |
| 7,591,803 B2 | 9/2009 | Bierman | |
| 7,594,910 B2 | 9/2009 | Butts et al. | |
| 7,635,355 B2 | 12/2009 | Bierman | |
| 7,722,571 B2 | 5/2010 | Bierman et al. | |
| 7,785,295 B2 | 8/2010 | Bierman | |
| 7,879,013 B2 | 2/2011 | Smith et al. | |
| 7,981,087 B2 | 7/2011 | Gesler | |
| 8,016,793 B2 | 9/2011 | Wright et al. | |
| 8,025,643 B2 | 9/2011 | Bierman | |
| 8,029,476 B2 | 10/2011 | Rosenberg et al. | |
| 8,052,648 B2 | 11/2011 | Dikerman et al. | |
| 8,052,649 B2 | 11/2011 | Wright | |
| 8,083,723 B2 | 12/2011 | Glenn | |
| 8,105,289 B2 | 1/2012 | Bierman et al. | |
| 8,105,290 B2 | 1/2012 | Wright et al. | |
| 8,114,054 B2 | 2/2012 | Bierman et al. | |
| 8,137,323 B2 | 3/2012 | Rosenberg et al. | |
| 8,177,756 B2 | 5/2012 | Wright | |
| 8,241,253 B2 | 8/2012 | Bracken | |
| 8,246,583 B2 | 8/2012 | Bierman | |
| 8,337,461 B2 | 12/2012 | Burkholz | |
| 8,394,066 B2 | 3/2013 | Rosenberg et al. | |
| 8,398,599 B2 | 3/2013 | Bierman | |
| 8,425,476 B2 | 4/2013 | Glenn | |
| 8,506,533 B2 | 8/2013 | Carlyon et al. | |
| 8,585,655 B2 | 11/2013 | Bierman | |
| 8,622,972 B2 | 1/2014 | Nystroem et al. | |
| 8,636,698 B2 | 1/2014 | Bierman et al. | |
| 8,657,791 B2 | 2/2014 | Bierman et al. | |
| 8,795,237 B2 | 8/2014 | Vitaris et al. | |
| 8,915,885 B2 | 12/2014 | Smith et al. | |
| 8,915,891 B2 | 12/2014 | Bomhoft | |
| 8,932,263 B2 | 1/2015 | Rosenberg et al. | |
| 8,979,805 B1 | 3/2015 | Khalaj | |
| 9,056,186 B2 | 6/2015 | Wright et al. | |
| 9,061,122 B2 | 6/2015 | Bierman et al. | |
| 9,314,596 B2 | 4/2016 | Rosenberg et al. | |
| 9,333,323 B2 | 5/2016 | Racz et al. | |
| 9,408,569 B2 | 6/2016 | Andreae et al. | |
| 9,433,754 B2 | 9/2016 | Mogg | |
| 9,480,821 B2 | 11/2016 | Ciccone et al. | |
| 9,486,613 B2 | 11/2016 | Dickert et al. | |
| 9,526,869 B2 | 12/2016 | Beran | |
| 9,545,502 B2 | 1/2017 | Maseda et al. | |
| 9,550,043 B2 | 1/2017 | Rosenberg et al. | |
| 9,550,044 B2 | 1/2017 | Maseda et al. | |
| 9,682,215 B2 | 6/2017 | Ashfaque | |
| 9,782,567 B2 | 10/2017 | Rosenberg et al. | |
| 10,105,085 B2 | 10/2018 | Andreae et al. | |
| 10,357,636 B2 | 7/2019 | Sonderegger et al. | |
| 10,426,929 B2 | 10/2019 | Burkholz et al. | |
| 2002/0165493 A1 | 11/2002 | Bierman | |
| 2005/0131351 A1 | 6/2005 | Bierman | |
| 2006/0084922 A1 | 4/2006 | Botha | |
| 2006/0217669 A1 | 9/2006 | Botha | |
| 2006/0270994 A1 | 11/2006 | Bierman | |
| 2007/0066958 A1 | 3/2007 | Wright | |
| 2007/0142782 A2 | 6/2007 | Bierman | |
| 2007/0149930 A1 | 6/2007 | Bierman | |
| 2008/0125718 A1 | 5/2008 | Tsuchiya et al. | |
| 2008/0200880 A1 | 8/2008 | Kyvik | |
| 2009/0149814 A1 | 6/2009 | Bailey | |
| 2009/0306602 A1 | 12/2009 | Elwell et al. | |
| 2010/0100049 A1 | 4/2010 | Godfrey | |
| 2010/0179481 A1 | 7/2010 | Bierman et al. | |
| 2010/0179563 A1 | 7/2010 | Skakoon et al. | |
| 2010/0298777 A1 | 11/2010 | Nishtala | |
| 2011/0213310 A1 | 9/2011 | Bierman | |
| 2011/0282291 A1 | 11/2011 | Ciccone | |
| 2012/0016312 A1 | 1/2012 | Brown et al. | |
| 2012/0041377 A1 | 2/2012 | Haak | |
| 2012/0059328 A1 | 3/2012 | Dikerman et al. | |
| 2012/0136314 A1 | 5/2012 | Ciccone et al. | |
| 2012/0271240 A1 | 10/2012 | Andino et al. | |
| 2013/0053785 A1 | 2/2013 | Paravatiyar et al. | |
| 2013/0138045 A1 | 5/2013 | Bierman | |
| 2014/0061408 A1 | 3/2014 | Heinecke et al. | |
| 2014/0200517 A1 | 7/2014 | Humphries et al. | |
| 2014/0343531 A1 | 11/2014 | Larkin | |
| 2015/0112270 A1 | 4/2015 | Smith et al. | |
| 2015/0119845 A1 | 4/2015 | Collins et al. | |
| 2015/0141962 A1 | 5/2015 | Collins et al. | |
| 2015/0217088 A1 | 8/2015 | Zyzelewski et al. | |
| 2015/0224286 A1 | 8/2015 | Teh et al. | |
| 2015/0367102 A1 | 12/2015 | Andino et al. | |
| 2016/0015932 A1 | 1/2016 | Catudal | |
| 2016/0184554 A1 | 6/2016 | Rosenberg et al. | |
| 2016/0354580 A1 | 12/2016 | Teoh et al. | |
| 2016/0367789 A1 | 12/2016 | Beran | |
| 2017/0043130 A1 | 2/2017 | Jones et al. | |
| 2017/0080187 A1 | 3/2017 | Maseda et al. | |
| 2017/0274182 A1 | 9/2017 | O'Bryan et al. | |
| 2017/0368312 A1 | 12/2017 | Rosenberg et al. | |
| 2018/0001059 A1 | 1/2018 | Rosenberg et al. | |
| 2018/0161543 A1 | 6/2018 | Burkholz | |
| 2018/0289921 A1 | 10/2018 | Burkholz | |
| 2018/0289922 A1 | 10/2018 | Burkholz | |
| 2018/0344983 A1 | 12/2018 | Funk et al. | |
| 2019/0160275 A1 | 5/2019 | Funk et al. | |

FOREIGN PATENT DOCUMENTS

| | | | | |
|---|---|---|---|---|
| GB | 2499286 A | * | 8/2013 | ............ A61M 25/02 |
| JP | 2004201904 A | | 7/2004 | |
| WO | 2017042359 A1 | | 3/2017 | |
| WO | 2018222671 A1 | | 12/2018 | |

\* cited by examiner

STABILIZATION DEVICES FOR VASCULAR ACCESS AND METHODS OF USING THE SAME

CROSS-REFERENCE TO RELATED APPLICATIONS

This application is a divisional of U.S. patent application Ser. No. 15/992,661 entitled "Stabilization Devices for Vascular Access and Methods of Using the Same", filed May 30, 2018, which claims priority to U.S. Provisional Patent Application Ser. No. 62/512,332 entitled, "Stabilization Devices for Vascular Access and Methods of Using the Same", filed May 30, 2017, the disclosures of each of which are incorporated herein by reference in its entirety.

BACKGROUND

The embodiments described herein relate generally to medical devices and, more particularly, to devices and methods for stabilizing vascular access devices such as intravenous catheters and/or extension sets.

Many medical procedures and/or surgical interventions include inserting an access device or fluid transfer device into a portion of the body. For example, catheters and/or other lumen-defining devices can be inserted into and/or through vascular structures to access portions of the body or to transfer fluids from or to a patient. In some instances, vascular access devices (VADs) such as, for example, peripheral intravenous catheters (PIVs), are inserted into patients (e.g., when a patient is hospitalized or during other medical procedures) and are designed and/or intended to remain within the patient for an extended period.

VADs typically include a catheter formed from a soft bio-reactive polymer that is partially disposed in the body and that is attached, at a proximal end (e.g., the end outside of the body) to a hub, which in turn, can provide an interface for attaching any suitable device. After placing the VAD (e.g., a PIV catheter or the like) within a vein (or artery) of the patient, it is often desirable to stabilize and/or secure the VAD relative to the patient. For example, in some instances, movement of the VAD relative to the patient can result in undesirable bending, flexing, and/or kinking of the catheter. In other instances, movement of the VAD (e.g., along a longitudinal axis of the VAD) can withdraw a portion of the catheter from the patient's body, which in turn, can expose that portion of the catheter to an unsterile environment. Moreover, moving the VAD back to its original position can disposed the potentially contaminated portion of the VAD catheter in the patient, thereby increasing the chances of infection.

Stabilizing and/or securing devices are often used in an effort to minimize movement of a placed or indwelling VAD (e.g., PIV catheter). Some known stabilizing and/or securing devices, however, are complicated and/or time consuming to use, while others may provide inadequate stabilization. In addition, the shape and/or configuration of some known stabilizing and/or securing devices can negatively impact a flow rate through a portion the VAD and/or the vein (or artery) in which the catheter is disposed.

Thus, a need exists for improved devices and methods for stabilizing placed vascular access devices.

SUMMARY

Devices and methods for stabilizing placed or indwelling vascular access devices such as, for example, intravenous or arterial catheters are described herein. In some embodiments, an apparatus includes a stabilization device configured to stabilize an access device when a distal end portion of the access device is inserted through a target location of a patient and at least partially disposed within a portion of the patient. The stabilization device can include a coupling surface, a proximal surface, and a base surface. The coupling surface is configured to be placed in contact with an adapter coupled to a proximal end portion of the access device. The proximal surface forms at least one angle and is configured to facilitate securement of the stabilization device to the target location of the patient. The base surface forms a contoured portion configured to be placed in contact with the target location and a recessed portion configured to be spaced apart from the target location when the contoured portion is in contact with the target location. The stabilization device is configured to be secured to the target location of the patient such that (1) the adapter is retained in a fixed position relative to the coupling surface and (2) the access device is stabilized relative to the target location.

DETAILED DESCRIPTION

Figure 1:
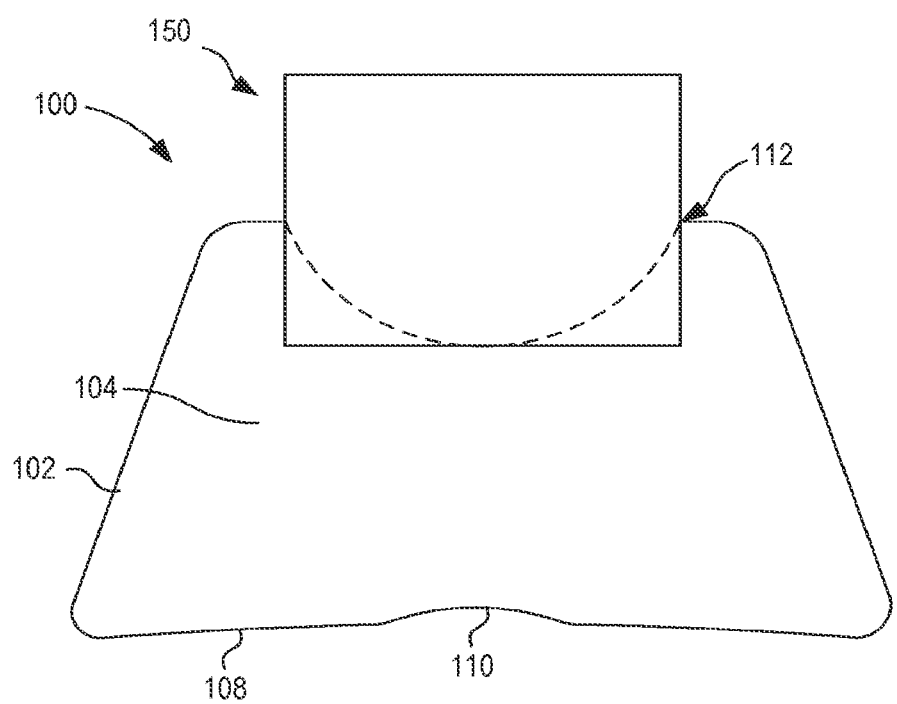
FIGS. 1 and 2 are a rear schematic illustration and a right-side schematic illustration, respectively, of a stabilization device according to an embodiment.

In some embodiments, an apparatus includes a stabilization device configured to stabilize an access device when a distal end portion of the access device is inserted through a target location of a patient and at least partially disposed within a portion of the patient. The stabilization device can include a coupling surface, a proximal surface, and a base surface. The coupling surface is configured to be placed in contact with an adapter coupled to a proximal end portion of the access device. The proximal surface forms at least one angle and is configured to facilitate securement of the stabilization device to the target location of the patient. The base surface forms a contoured portion configured to be placed in contact with the target location and a recessed portion configured to be spaced apart from the target location when the contoured portion is in contact with the target location. The stabilization device is configured to be secured to the target location of the patient such that (1) the adapter is retained in a fixed position relative to the coupling surface and (2) the access device is stabilized relative to the target location.

In some embodiments, an apparatus includes a stabilization device configured to stabilize a vascular access device at least partially disposed within a vein of a patient. The stabilization device includes a base surface and a coupling surface. The base surface forms a contoured portion configured to be placed in contact with a target location of the patient and a recessed portion configured to be at least partially aligned with and spaced apart from the vein of the patient when the contoured portion is in contact with the target location. The coupling surface is configured to be placed in contact with an adapter coupled to a proximal end portion of the vascular access device. The coupling surface includes a first portion and a second portion. The first portion includes at least one protrusion configured to selectively engage the adapter such that (1) a portion of the adapter is aligned with and configured to be placed in contact with the second portion of the coupling surface when the first portion of the coupling surface is in contact with a distal end portion of the adapter, and (2) the portion of the adapter is misaligned with and spaced apart from the second portion of the coupling surface when the first portion of the coupling surface is in contact with a proximal end portion of the adapter.

In some embodiments, a method of stabilizing a vascular access device at least partially disposed within a vein of a patient includes coupling a stabilization device to the vascular access device at least partially disposed in the vein of the patient. The stabilization device is positioned on a target location of the patient such that a recessed portion formed by a base surface of the stabilization device is aligned with the vein. A first strip of medical tape is applied to a proximal surface of the stabilization device such that each of a first end portion and a second end portion of the first strip of medical tape are in contact with the target location of the patient and are distal to a medial portion of the medical tape. The medial portion of the first strip of medical tape is at least partially in contact with the proximal surface of the stabilization device and at least partially in contact with the target location of the patient. A second strip of medical tape is applied to a portion of the stabilization device distal to the proximal surface such that the second strip of medical tape partially overlaps at least the first end portion and the second end portion of the first strip of medical tape.

In some embodiments, a stabilization device has a proximal end portion and a distal end portion and is configured to be secured to the skin of a patient. The proximal end portion includes a proximal surface forming at least one angle configured to facilitate securement of the stabilization device to the skin of the patient. A base surface of the stabilization device forms a contour that is configured to be placed in contact with the skin of a patient, and defines a recess along the contour configured to be spaced apart from the skin of the patient. The stabilization device is configured to couple to at least one of a hub of a placed vascular access device or an adapter coupled to the placed vascular access device to stabilize the placed vascular access device when the stabilization device is secured to the skin of the patient.

As used in this specification, the singular forms "a," "an," and "the" include plural referents unless the context clearly dictates otherwise. Thus, for example, the term "a member" is intended to mean a single member or a combination of members, "a material" is intended to mean one or more materials or a combination thereof, "a device" is intended to mean a single device or a combination of devices.

As used herein, the terms "about" and "approximately" can be used interchangeably and generally mean plus or minus 10% of the value stated. For example, about 0.5 would include 0.45 and 0.55, about 10 would include 9 to 11, about 1000 would include 900 to 1100.

Similarly, the term "substantially" when used in connection with a geometric construction and/or geometric relationship is intended to convey that the structure and/or relationship so defined is nominally the recited structure and/or relationship. As one example, a first portion of a stabilization device that is described as being "substantially perpendicular" to a second portion of the stabilization device is intended to convey that, although a perpendicular relationship (e.g., being arranged, disposed at, and/or otherwise forming a 90° angle or orientation) is desirable, some variance or non-perpendicularity can occur in a "substantially perpendicular" relationship. As another example, two geometric constructs that are described as being substantially aligned is intended to convey that, although alignment of the geometric constructs is desirable, some variance or misalignment can occur. In some instances, variances such as those described above can result from, for example, manufacturing tolerances, or other practical considerations. Thus, a geometric construction modified by the term "substantially" includes such geometric properties within a tolerance of plus or minus 5% of the stated geometric construction. For example, a "substantially perpendicular" relationship is a relationship between two geometric constructs that is within plus or minus 5% of being perpendicular.

As used herein, the term "set" can refer to multiple features or a singular feature with multiple parts. For example, when referring to a set of protrusions, the set of protrusions can be considered as one protrusion with multiple portions, or the set of protrusions can be considered as multiple, distinct protrusions. Thus, a monolithically constructed item can include a set of protrusions. Such a "set" may include multiple portions and/or components that are either continuous or discontinuous from each other. Moreover, a "set" can also be formed from multiple components that are produced separately and are later joined together (e.g., via a weld, an adhesive, or any suitable method).

The devices and methods described herein are configured to stabilize devices and/or components of devices that are directly or indirectly inserted in a patient. Such devices are generally referred to herein as vascular access devices (VADs). Non-limiting examples of a VAD can include intravenous (IV) access devices such as peripheral intravenous catheters (PIV), peripheral intravenous central catheters (PICCs or PIC lines), midline catheters, extended dwell catheters (EDCs), etc. In other embodiments, a VAD can be an intra-arterial access device such as an arterial line, and/or the like. While reference to use with specific access devices is made herein, it should be understood that such reference is presented by way of example and not limitation.

As used herein, the term "catheter" describes an element configured to define a passageway such as a cannula, a tube, or other lumen-defining structure. In some instances, a catheter can be used for moving a bodily fluid from a first location to a second location (e.g., a fluid passageway to move a bodily fluid out of the body). While cannulas can be configured to receive a trocar, a guide wire, or an introducer to deliver the cannula to a volume inside the body of a patient, the catheters and/or cannulas referred to herein need not include or receive a trocar, guide wire, or introducer and can be positioned and/or inserted into, for example, the vasculature of a patient using any suitable method.

As used in this specification, the term "extension set" generally refers to a device or adapter that is coupled to a hub of a VAD such as a peripheral IV catheter or the like. The "extension sets" can be any suitable configuration. For example, in some embodiments, an extension set can be a single port or a multi-port adapter. As a specific example, an extension set can be and/or can refer to a "Y-shaped" dual port extension. In other embodiments, an extension set can be and/or can refer to a "T-shaped" dual port extension set.

In general, some known extension sets are configured to couple between a hub of a VAD and/or any suitable medical device and can allow one or more objects, devices, medicaments, fluids, etc. to access a portion of the body of a patient (e.g., via the VAD). More particularly, in some instances, an extension set can be coupled to an indwelling access device (e.g., a PIV or the like) and can facilitate the transfer and/or collection of one of more fluids. In some instances, the fluid can be a bodily fluid including, but not limited to, blood, cerebrospinal fluid, urine, bile, lymph, saliva, synovial fluid, serous fluid, pleural fluid, amniotic fluid, mucus, vitreous, air, and the like, or any combination thereof.

In some embodiments, any of the extension sets described herein can be a commercially available extension set. That is to say, in some embodiments, and of the stabilization devices described herein can be configured for use with a commercially available extension set. In other embodiments, any of the stabilization devices described herein can be configured for use with a custom extension set and/or an extension set configured for specific use with the stabilizer devices described herein. Accordingly, it should be understood, that the term "extension set" is provided by way of example only and not limitation.

As used in this specification, the words "proximal" and "distal" refer to the direction closer to and away from, respectively, a user who would place the device into contact with a patient. Thus, for example, the end of a device first touching the body of the patient would be the distal end, while the opposite end of the device (e.g., the end of the device being manipulated by the user) would be the proximal end of the device. Moreover, the terms "proximal" and "distal" when referring to a position of a construct or the like can be used to describe, for example, a relative position the construct so described. For example, a first portion of a device can be said to be in a distal position relative to second portion of the device when the position of the first portion of the device is further from the user of the device than the position of the second portion of the device.

Figure 2:
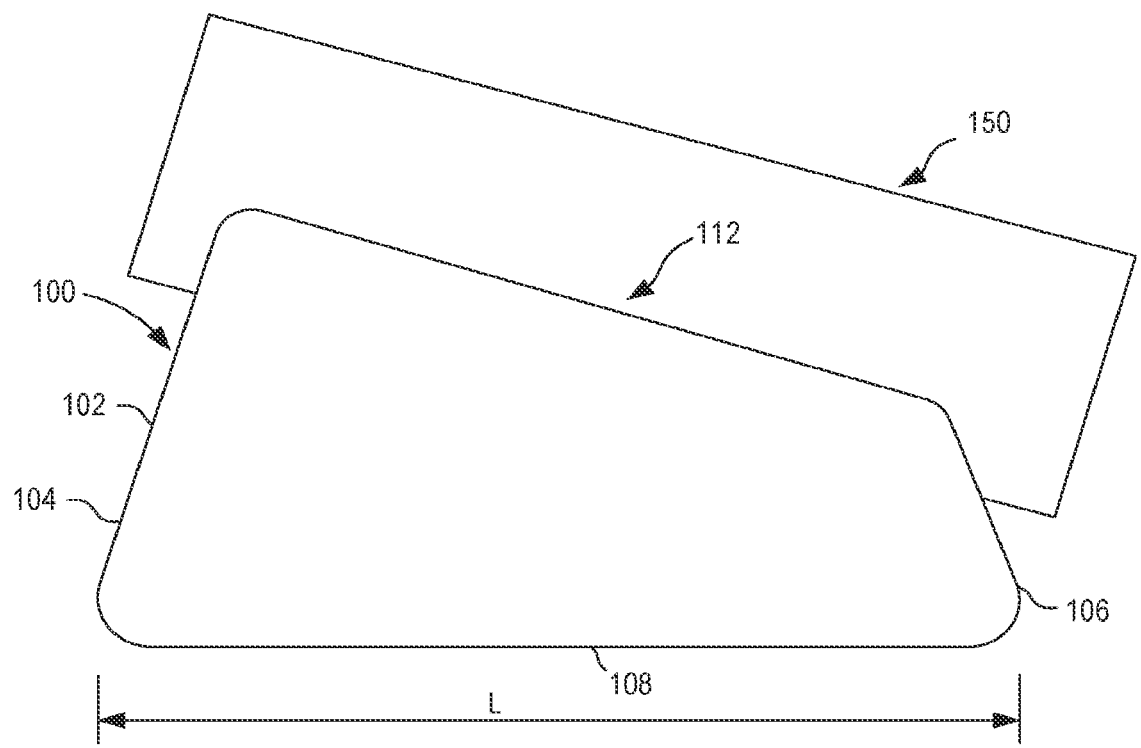
Figure 3:
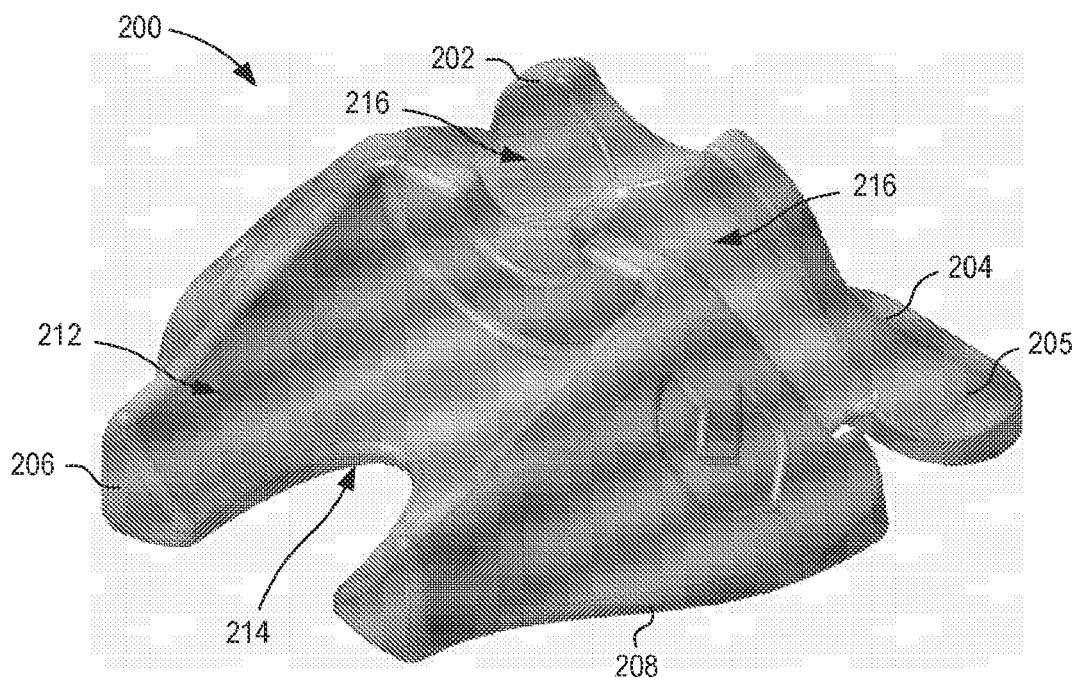
FIGS. 3-6 are various views of a stabilization device according to an embodiment.

FIGS. 1 and 2 are schematic illustrations of a stabilization device 100 according to an embodiment. The stabilization device 100 is configured to be placed in contact with the skin of a patient at or near an insertion site of an indwelling or placed vascular access device (VAD) such as those described above. The stabilization device 100 is configured to couple to and/or otherwise engage the VAD and/or a device coupled to the VAD. Once coupled to the VAD and/or the device coupled to the VAD, the stabilization device 100 can be secured to the skin of the patient, which in turn, secures and/or stabilizes at least a portion of the VAD relative to the patient, as described in further detail herein.

The stabilization device 100 can be any suitable shape, size, and/or configuration. As shown in FIGS. 1 and 2, the stabilization device 100 has a proximal end portion 102 and a distal end portion 106, and has a base surface 108 and a coupling surface 112. The proximal end portion 102 has a proximal surface 104 that has a predetermined and/or desired shape. For example, in some embodiments, the proximal surface 104 can be angled, tapered, flared, curved, rounded, and/or the like. As described in further detail herein, the arrangement and/or shape of the proximal surface 104 can facilitate the coupling or securing of the stabilization device 100 to the skin of the patient (e.g., via medical tape or the like).

The base surface 108 can be any suitable shape and/or configuration. For example, the base surface 108 can have a contour and/or shape that is generally concave. In some embodiments, the concave contour and/or shape can be based at least in part on a curvature and/or shape of a portion of the patient's anatomy. For example, in some embodiments, the base surface 108 can have a contour and/or shape that is based at least in part on a general contour and/or curvature of a patient's hand or forearm (or other suitable IV insertion site). In some embodiments, forming the contour and/or shape of the base surface 108 to be similar to and/or at least partially based on the curvature of an IV insertion site of the patient can, for example, increase a surface area of the base surface 108 that is in contact with the skin of the patient, which in turn, can increase the stability of the stabilization device 100 when secured to the skin of the patient, as described in further detail herein.

As shown in FIG. 1, the base surface 108 defines a recess 110 (e.g., a notch, indentation, cutout, etc.) that extends along the base surface 108 in the direction of a longitudinal axis of the stabilization device 100. In other words, the recess 110 extends along the base surface 108 in a proximal-distal direction. In some embodiments, the recess 110 extends along the base surface 108 through the proximal end portion 102 and through the distal end portion 106 (e.g., along the length L of the base surface 108 (FIG. 2)). In some embodiments, when the base surface 108 of the stabilization device 100 is placed in contact with the skin of the patient, the recess 110 can be spaced apart from the skin of the patient (e.g., not in contact with the skin of the patient). In other embodiments, the base surface 108 including the recess 110 can be in contact with the skin of the patient.

The stabilization device 100 is configured to be placed in a position along the skin of the patient such that the recess 110 is aligned with and/or otherwise disposed over a vein of the patient. In some instances, the stabilization device 100 can be placed on the skin of the patient at or near an insertion site (also referred to as a "target location") of, for example, an IV catheter. More specifically, the stabilization device 100 is configured to be positioned on the skin of the patient such that the recess 110 is disposed over the vein in which the VAD (e.g., the indwelling IV catheter, arterial catheter, or the like) is disposed. In some instances, such an arrangement can reduce an amount of force exerted by the base surface 108 on the vein, which might otherwise result in a reduced flow rate through at least a portion of the vein. For example, in embodiments in which the recess 110 is spaced apart from the skin of the patient, the stabilization device 100 does not (or substantially does not) exert a force on the vein in which the VAD is disposed. In other embodiments (e.g., when the recess 110 is in contact with the skin of the patient), a force exerted on by the recess 110 on the vein in which the VAD is disposed can be less than a force exerted by other portions of the base surface 108 (e.g., non-recess portions) on or near an area of the patient surrounding the vein.

The coupling surface 112 of the stabilization device 100 can be any suitable shape, size, and/or configuration. In some embodiments, the coupling surface 112 can form a contour or shape that is at least partially based on a shape of a vascular access device (VAD) 150 (or a hub thereof) and/or a device coupled to a VAD (e.g., an extension set or the like). In some embodiments, the coupling surface 112 can be configured to contact and/or engage an outer surface of the VAD 150 to form and/or define a friction fit therebetween. That is to say, the coupling surface 112 can have a size and/or shape that is slightly undersized relative to the VAD 150 to form a friction fit, press fit, interference fit, etc. when the VAD 150 is in contact with the coupling surface 112.

In some embodiments, the shape and/or contour of the coupling surface 112 can be configured to dispose the VAD 150 at a predetermined, predefined, and/or otherwise desired angle relative to the skin of the patient at or near the insertion site of the VAD 150. For example, in some embodiments, the coupling surface 112 can be angled such that a height of the coupling surface 112 at or near the proximal end portion 102 is greater than a height of the coupling surface 112 at or near the distal end portion 106. In some embodiments, the coupling surface 112 of the stabilization device 100 can be arranged to secure the VAD 150 at any suitable angle based at least in part on an angle of insertion of, for example, the VAD 150 or a catheter thereof. For example, in some embodiments, the coupling surface 112 can be configured to dispose the V AD 150 at an angle that can minimize a risk or likelihood of the VAD 150 (e.g., a catheter of the VAD 150) becoming kinked.

As described above, the stabilization device 100 can be used to secure, for example, a device coupled to a vascular access device. By way of example, in some embodiments, the stabilization device 100 can be configured to couple to and/or secure an IV extension set, which in turn is coupled to an indwelling or placed intravenous catheter. Although not shown in FIGS. 1 and 2, in such embodiments, the coupling surface 112 can have a shape and/or contour that is configured and/or suitable for use with a dual port extension set such as a Y-shaped extension set, T-shaped extension set, and/or the like. For example, in some embodiments, the coupling surface 112 can have a side channel or the like configured to receive one of the ports of such an extension set (e.g., a side port of a T-shaped extension set). In some embodiments, the side channel or the like can be configured to extend substantially perpendicularly relative to the coupling surface 112 and/or the other portions of the coupling surface 112.

As described above, the stabilization device 100 is configured to secure and/or stabilize the VAD 150 to, for example, the skin of a patient. For example, in some instances, an IV catheter (e.g., the VAD 150) can be inserted into the hand of a patient such that (1) a portion of the IV catheter is disposed within a vein and (2) a hub of the IV catheter is disposed outside of the patient. In some instances, an extension set (e.g., a T-adapter, Y-adapter, and/or the like) can be coupled to the hub of the IV catheter. With the extension set coupled to the IV hub, a user (e.g., a doctor, nurse, technician, physician, surgeon, and/or other medical professional) can manipulate the stabilization device 100 by placing a portion of the extension set (e.g., represented in FIGS. 1 and 2 as the VAD 150) in contact with the coupling surface 112 of the stabilization device 100. As described above, the coupling surface 112 can be configured to form a friction fit and/or the like with the portion of the extension set to couple the extension set to the stabilization device 100. Although the extension set is described above as being coupled to the IV hub prior to being coupled to the stabilization device 100, in other embodiments, the stabilization device 100 can be placed in a desired position and/or the extension set can be coupled to the stabilization device 100 prior to coupling the extension set to the IV hub.

Once the stabilization device 100 is coupled to the extension set, the stabilization device 100 can be positioned on the skin of the patient (e.g., at or near the insertion site). In this example, the IV catheter is inserted into the hand of the patient and thus, the stabilization device 100 is position relative to the hand of the patient. Thus, the base surface 108 of the stabilization device 100 can be placed in contact with the skin of the patient at or near the insertion site (e.g., the site at which the VAD 150 or IV catheter enters the patient). In some instances, the stabilization device 100 can be adjusted and/or positioned such that the recess 110 is aligned with and/or otherwise disposed about or over the vein in which the IV catheter is disposed, as described above.

Having coupled the stabilization device 100 to the extension set and having placed the stabilization device 100 in the desired position at or near the insertion site, the user can secure the stabilization device 100 to the patient. In some embodiments, the user can secure the stabilization device 100 via medical tape or the like. For example, a user can remove a strip of medical tape from a roll of medical tape (e.g., a first strip of medical tape) and can apply the strip of medical tape to the proximal surface 104 of the stabilization device 100 (not shown in FIGS. 1 and 2) such that a first portion of the medical tape is adhered to the proximal surface 104 and a second portion of the medical tape is adhered to the skin of the patient. In some instances, the user can substantially center the medical tape relative to the proximal surface 104. As described above, the proximal surface 104 can have a shape, size, and/or configuration that facilitates the securement of the stabilization device 100. For example, in some embodiments, the proximal surface 104 can be angled and/or can have a relatively curved contour or the like such that when the user applies the medical tape to the proximal surface 104, the tape curves, bends, conforms, and/or otherwise forms a shape and/or follows a path that is at least partially based on the shape of the proximal surface 104. As described in further detail herein, in some embodiments, the arrangement of the proximal surface 104 can be such that end portions of the tape are adhered to the skin of the patient and positioned distal to the proximal surface 104.

In some instances, the user can remove a second strip of medical tape (not shown in FIGS. 1 and 2) from the roll of medical tape and can apply the second strip of medical tape transversely across a portion of the stabilization device 100 and the VAD 150. In some instances, the user can apply the second strip of medical tape such that a first end portion of the medical tape is adhered to a portion of the patient's skin on a first side of the stabilization device 100; a second end portion of the medical tape is adhered to a portion of the patient's skin on a second side of the stabilization device 100 substantially opposite the first side of the stabilization device 100; and a medial portion (e.g., between the first end portion and the second end portion) is adhered to at least one of the stabilization device 100 or the VAD 150. Moreover, the first end portion of the second strip of medical tape can at least partially overlap a first end portion of the first strip of medical tape and the second end portion of the second strip of medical tape can at least partially overlap a second end portion of the first strip of medical tape.

Although the first strip of medical tape and the second strip of tape are described as being applied in a specific order, it should be understood that the strips of medical tape can be applied to the stabilization device 100 and the VAD 150 in any suitable order. For example, in some instances, the user can apply the second strip of medical tape transversely across the portion of the stabilization device 100 and the VAD 150 (as described above) and then can apply the first strip of medical tape to the proximal surface 104 of the stabilization device 100 (as described above). Thus, in such instances, a portion of the first strip of medical tape overlaps a portion of the second strip of medical tape.

Securing the stabilization device 100 to the skin of the patient (e.g., via the medical tape) results in the stabilization device 100 and/or the medical tape securing, stabilizing, and/or substantially immobilizing the VAD 150 relative to the patient. That is to say, the arrangement of the stabilization device 100 is such that securing the stabilization device 100 and the VAD 150 to the skin of the patient can reduce and/or substantially prevent movement of the VAD 150 or at least an IV catheter thereof relative to the vein in which the IV catheter is at least partially disposed, as described in further detail herein with respect to a specific embodiment. Moreover, the arrangement of the recess 110 along the base surface 108 can reduce and/or can substantially eliminate a force otherwise exerted on the vein in which the VAD 150 (e.g., IV catheter or the like) is disposed.

FIGS. 3-9 illustrate a stabilization device 200 according to an embodiment. As described above with reference to the stabilization device 100, the stabilization device 200 is configured to be placed in contact with the skin of a patient at or near an insertion site of an indwelling or placed vascular access device (VAD). The stabilization device 200 is configured to couple to and/or otherwise engage the VAD and/or a device coupled to the VAD (e.g., an extension set). Once coupled to the VAD and/or the device coupled to the VAD, the stabilization device 200 can be secured to the skin of the patient, which in turn, secures and/or stabilizes at least a portion of the VAD relative to the patient, as described in further detail herein.

The stabilization device 200 can be any suitable shape, size, and/or configuration. For example, in some embodiments, the stabilization device 200 can have a size and/or shape that is based at least in part on a size and/or shape of the VAD to be stabilized. In some embodiments, the size and/or shape of the stabilization device 200 can facilitate ease of use, for example, by simplifying a process of securing the stabilization device 200 to the skin of a patient. In some embodiments, the size and/or shape of the stabilization device 200 can increase ergonomics, grip, and/or the like. For example, in some embodiments, the stabilization device 200 and/or a portion thereof can allow a user maintain a secure grip on the stabilization device 200 as the user couples (or decouples) one or more devices to a VAD, an extension set, and/or any other suitable device being stabilized. In some instances, maintaining a secure grip during such a coupling or decoupling process can limit a force exerted on the stabilization device 200 that may otherwise be sufficient to move the stabilization device 200 relative to a target location on the patient (e.g., an IV catheter insertion site). In other words, the size and/or shape of the stabilization device 200 can allow it to stabilize, secure, and/or substantially immobilize a VAD coupled thereto as the user couples or decouples a device (e.g., a fluid transfer device or the like) to the VAD.

As shown in FIGS. 3-6, the stabilization device 200 has a proximal end portion 202 and a distal end portion 206, and has a base surface 208 and a coupling surface 212. In general, the coupling surface 212 is configured to receive, retain, and/or otherwise couple to an extension set 260 such as, for example, a T-adapter or T-connector, which in turn is coupled to an indwelling or placed VAD. In this embodiment, the indwelling or placed VAD can be, for example, an IV catheter 250 (see e.g., FIGS. 7-9). The base surface 208 is configured to be placed in contact with the skin of a patient in a predetermined and/or desired manner at or near an insertion site of the IV catheter 250 or the like (also referred to herein as a "target location"). Once the stabilization device 200 is coupled to the extension set 260 and the base surface 208 is in contact with the skin of the patient at or near the insertion site, the stabilization device 200 (and the extension set 260) can be secured to the skin of the patient (see e.g., FIGS. 7 and 8) to secure and/or stabilize at least a portion of the IV catheter 250 relative to the patient and/or the vein in which the IV catheter 250 is disposed, as described in further detail herein.

The proximal end portion 202 has a proximal surface 204 that has a predetermined and/or desired shape. For example, the proximal surface 204 can be angled, tapered, flared, curved, rounded, and/or the like. In the embodiment shown in FIGS. 3-9, the proximal surface 204 can have a rounded, curved, parabolic, and/or substantially bell-shaped perimeter. Moreover, the proximal end portion 202 and/or the proximal surface 204 can include a set of extensions 205 (e.g., feet, tabs, pads, protrusions, etc.) that extend transversely away from a center of the stabilization device 200. As described in further detail herein, the arrangement and/or shape of the proximal surface 204 and/or the extensions 205 can facilitate the coupling or securing of the stabilization device 200 to the skin of the patient (e.g., via medical tape or the like).

Figure 4:
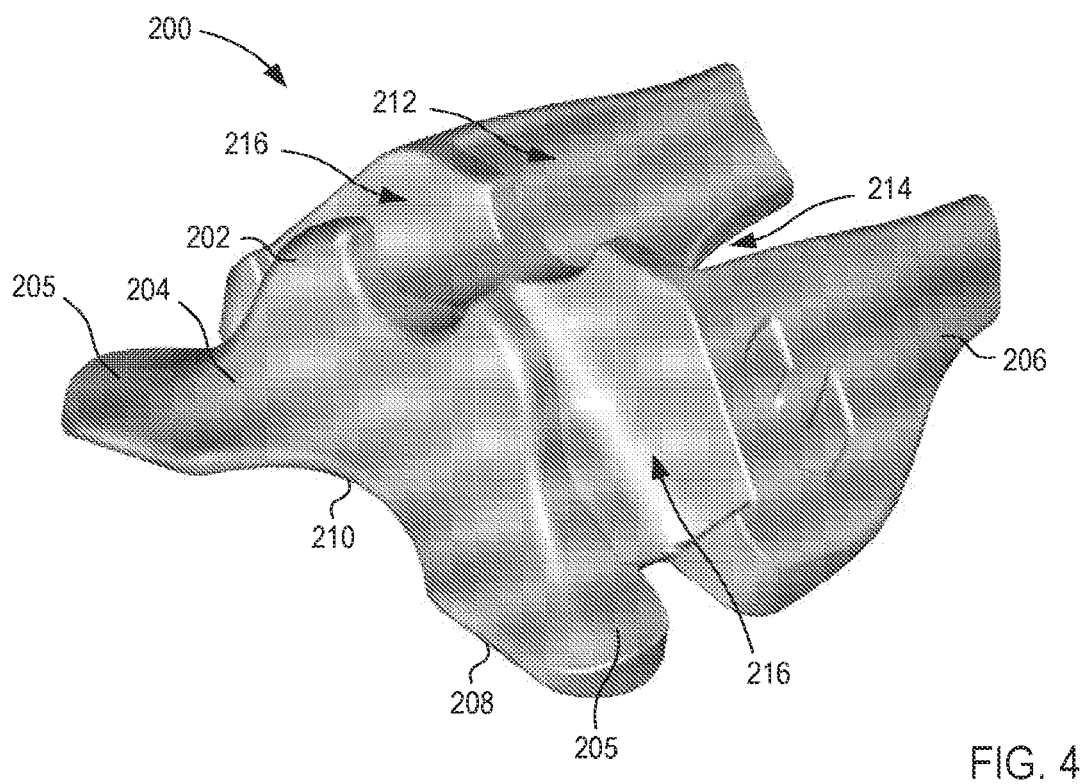
Figure 5:
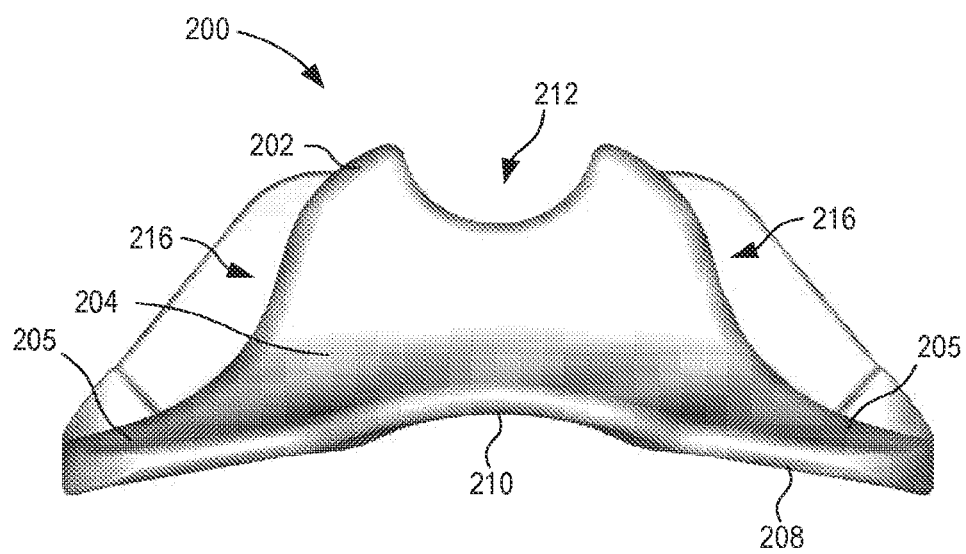
Figure 6:
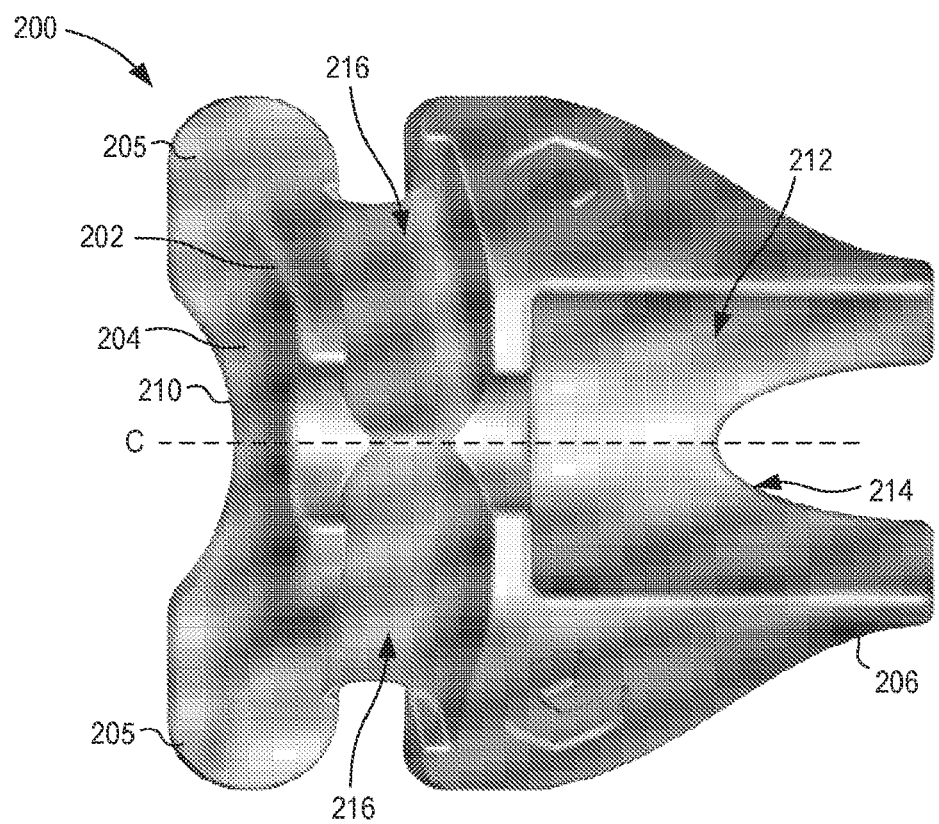

The base surface 208 can be any suitable shape and/or configuration. For example, as shown in FIGS. 4 and 5, the base surface 208 can have a contour and/or shape that is generally concave. In some embodiments, the concave contour and/or shape can be based at least in part on a curvature and/or shape of a portion of the patient's anatomy. For example, in some embodiments, the base surface 208 can have a contour and/or shape that is based at least in part on a general contour and/or curvature of a patient's hand or forearm (or other suitable insertion site and/or target location). In some embodiments, forming the contour and/or shape of the base surface 208 to be similar to and/or at least partially based on the curvature of target location of the patient can, for example, increase a surface area of the base surface 208 that is in contact with the skin of the patient, which in turn, can increase the stability of the stabilization device 200 when secured to the skin of the patient, as described in further detail herein.

As shown in FIGS. 4 and 5, the base surface 208 defines a recess 210 (e.g., a notch, indentation, cutout, etc.) that extends along the base surface 208 in the direction of a longitudinal centerline of the stabilization device 200. In other words, the recess 210 extends along the base surface 208 in a proximal-distal direction. In some embodiments, the recess 210 extends along the base surface 208 through the proximal end portion 202 and through the distal end portion 206, as described above with reference to the stabilization device 100 shown in FIG. 2. In some embodiments, the recess 210 can have and/or can form a curved cross-sectional shape with a constant or a variable radius of curvature. For example, in some embodiments, the recess 210 can have and/or can form a parabolic cross-sectional shape. In other embodiments, the recess 210 can have and/or can form any suitable cross-sectional shape such as, for example, a V-shape, a U-shape, a W-shape, and/or any other suitable cross-sectional shape. In some embodiments, the size and/or shape of the recess 210 can be substantially constant along a length of the stabilization device 200. In other embodiments, the size and/or shape of the recess 210 can vary along the length of the stabilization device 200. For example, in some embodiments, the recess 210 can be tapered, decreasing in size and/or shape from a first size at the proximal end portion 202 to a second size at the distal end portion 206 (or vice versa).

The stabilization device 200 is configured to be placed in a position along the skin of the patient such that the recess 210 is aligned with and/or otherwise disposed over the vein in which the IV catheter 250 is disposed. In some embodiments, when the base surface 208 of the stabilization device 200 is placed in contact with the skin of the patient, the recess 210 can be spaced apart from the skin of the patient (e.g., not in contact with the skin of the patient). In other embodiments, the base surface 208 including the recess 210 can be in contact with a portion of the skin of the patient. In some embodiments, the recess 210 can have a height (or depth) and a width that are each larger than a diameter of the vein in which the IV catheter 250 is to be disposed. In other words, a size and/or shape of the recess 210 can be based at least in part on a size and/or shape of a vein over which the stabilization device 200 is disposed. For example, in some embodiments, the recess 210 can have a height or depth that is approximately 0.5 millimeters (mm) to approximately 3.0 mm and a width that is approximately 5.0 mm to approximately 40.0 mm. As one example, a recess 210 can have a height or depth that is approximately 2.0 mm and a width that is approximately 20 mm.

While the recess 210 is particularly shown in, for example, FIGS. 4 and 5, in some embodiments, the recess 210 can have any suitable size and/or shape. In some embodiments, the size and/or shape of the recess 210 can account for variations in vein size, shape, and/or path. For example, in some instances, a vein in which the IV catheter 250 is disposed can have one or more branch vessels coupled thereto, can extend in a non-linear or curved path, can extend at an angle, and/or otherwise can vary in size, shape, and/or arrangement between patients. As such, the recess 210 can have a width that is sufficiently large to allow the recess 210 to be disposed over a vein that can vary in size, shape, and/or arrangement. In some embodiments, for example, the recess 210 can have a width that is slightly smaller than a width of the base surface 208. In such embodiments, a relatively thin portion of the base surface 208 can be disposed on opposite sides of the recess 210. In other embodiments, the base surface 208 can include two parallel or substantially parallel protrusions, bumps, ridges, rails, etc. that that collectively define a space therebetween. In such embodiments, the portion of the base surface 208 disposed between the two protrusions or the like can form and/or can function similar to the recess 210.

In some embodiments, forming and/or defining the recess 210 to be larger (e.g., in height and/or width) than the vein in which the IV catheter 250 is disposed can, for example, reduce an amount of force that would otherwise be exerted by the base surface 208 on the vein. In some instances, such a force exerted by the base surface 208 on the vein may be sufficient to reduce a flow of blood within the vein. In some specific instances, such a reduction in flow may negatively impact the ability to withdraw blood from the vein and/or may impede the delivery of fluids into the vein. Accordingly, forming the recess 210 in the base surface 208 is such that the stabilization device 200 does not (or substantially does not) exert a force on the vein in which the IV catheter 250 is disposed, thereby allowing the stabilization device 200 to secure and stabilize the IV catheter 250 without substantially impeding a flow of fluid through the vein.

While the recess 210 is described above as being configured to reduce and/or substantially remove a force exerted on the vein in which the IV catheter 250 is disposed, in some embodiments, the recess 210 can allow for movement and/or reconfiguration of a portion of the patient while continuing to provide stabilization to or for the IV catheter 250. For example, in some embodiments, an IV catheter (e.g., the IV catheter 250) can be inserted into a patient's cephalic or basilic vein and a stabilization device 200 (e.g., the stabilization device 200) can be secured to the patient's antecubital fossa region. In some instances, bending of the patient's arm (e.g., at the elbow) can result in a change in tension, stress, and/or strain of the skin both in a circumferential direction and an axial direction along the patient's arm. In some instances, such a change in tension or the like can result in a bunching or bulging of skin at or near the antecubital fossa region. In some instances, such a bunching or bulging of skin can result in undesired lifting or movement of a stabilization device relative to an IV insertion site, which in turn, can result in undesired movement, bending, kinking, etc. of the IV catheter disposed in the vein.

In some embodiments, however, the arrangement of the recess 210 of the stabilization device 200 can allow at least a portion of the skin to bunch or bulge in a space defined by the recess 210, thereby at least partially filling the void of the recess 210 and reducing and/or substantially preventing undesired lifting or movement of the stabilization device 200. In other words, in some instances, the arrangement of the stabilization device 200 can be such that the stabilization device 200 stabilizes, secures, and/or substantially immobilizes the IV catheter 250 despite at least some movement of the patient. Moreover, in some embodiments, the recess 210 can extend along the width of the stabilization device 200 such that only the edges of the base surface 208 and/or only protrusions extending from the base surface 208 are in contact with the skin. In such embodiments, this arrangement can allow the skin to shift and stretch axially underneath and to either side of the stabilization device 200 as shear forces are applied by movement of the skin, thereby reducing the amount of force that can otherwise result in lateral movement of the stabilization device 200 relative to the insertion site and/or target location.

The coupling surface 212 of the stabilization device 200 can be any suitable shape, size, and/or configuration. In the embodiment shown in FIGS. 3-9, the coupling surface 212 can form a contour or shape that is at least partially based on a shape of the extension set 260. In some embodiments, the coupling surface 212 can be configured to contact and/or engage an outer surface of the extension set 260 to form and/or define a friction fit therebetween. That is to say, the coupling surface 212 can have a size and/or shape that is slightly undersized relative to the extension set 260 to form a friction fit, press fit, interference fit, etc. when the extension set 260 is in contact with the coupling surface 212.

Figure 7:
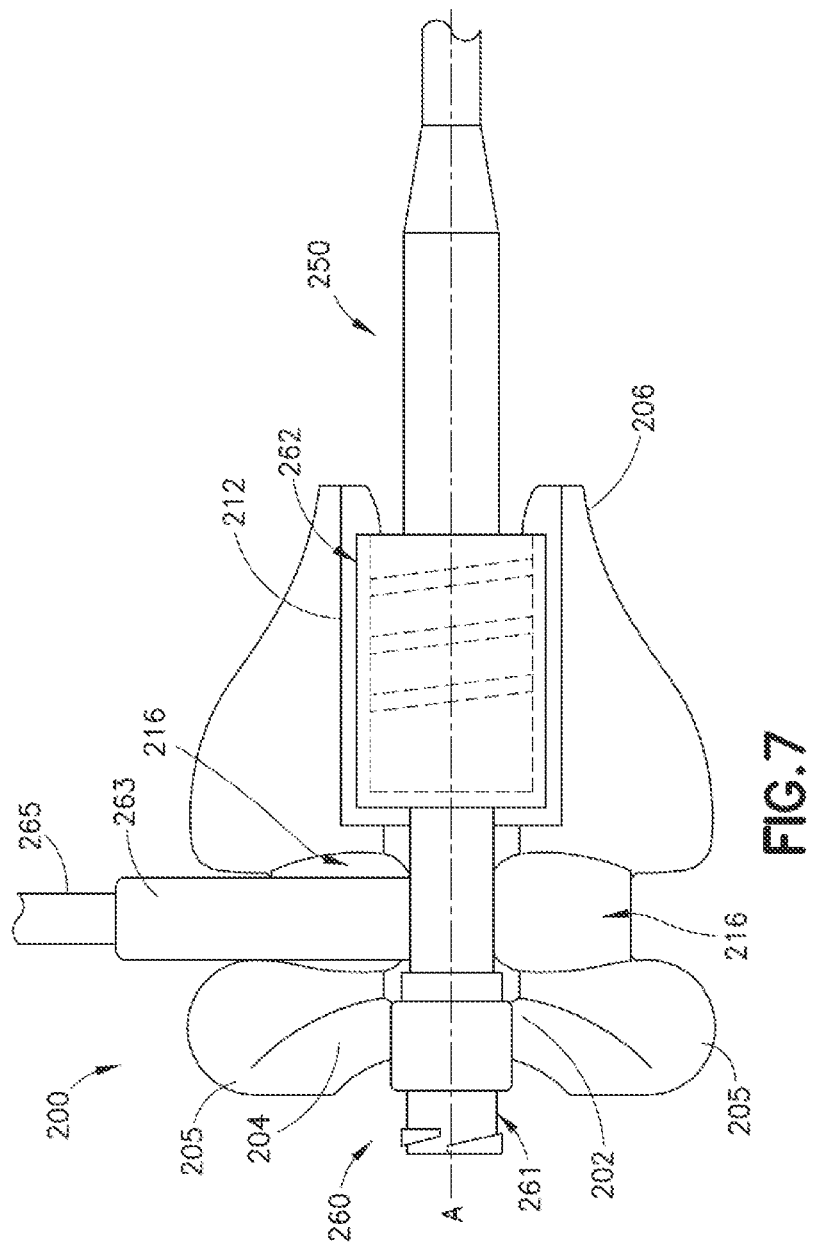
FIG. 7 is a top view of the stabilization device of FIG. 3 coupled to a vascular access device.

In the embodiment shown in FIGS. 3-9, the coupling surface 212 can be configured to receive and/or couple to a T-shaped adapter or connector (e.g., the extension set 260). For example, the coupling surface 212 includes a distal notch 214 and one or more side channels 216. The distal notch 214 formed by and/or along the coupling surface 212 can be configured to accommodate a distal locking mechanism 262 (e.g., a Luer Lok®) of the extension set 260. For example, in some embodiments, the extension set 260 (e.g., the T-adapter) can include a rotatable lock at a distal end portion thereof that is configured to physically and fluidically couple the extension set 260 to the IV catheter 250. Accordingly, the distal notch 214 can provide sufficient space for a user to grasp and rotate the rotatable lock to couple or decouple the distal locking mechanism 262 of the extension set 260 to or from the IV catheter 250. Moreover, the extension set 260 can couple to the coupling surface 212 such that a proximal locking mechanism 261 of the extension set 260 is proximal to the proximal surface 204 of the stabilization device 200, as shown in FIG. 7. In some embodiments, such an arrangement can facilitate the coupling or decoupling of one or more devices (e.g., a fluid transfer device, syringe, fluid reservoir, etc.) to or from the proximal locking mechanism 261 of the extension set 260.

The one or more side channels 216 of the stabilization device 200 can be any suitable shape, size, and/or configuration. In the embodiment shown in FIGS. 3-9, the stabilization device 200 includes two side channels 216, with one side channel 216 on opposite sides of the stabilization device 200 and extending in a perpendicular and/or transverse direction relative to, for example, a longitudinal centerline C of the stabilization device 200 (see e.g., FIG. 6). At least one of the side channels 216 is configured to receive a side port 263 of the extension set 260 (see e.g., FIG. 7). For example, in the embodiment shown in FIGS. 3-9, the extension set 260 is a dual port extension set having a "T" configuration in which the side port 263 is substantially perpendicular to a longitudinal axis A defined between the proximal locking mechanism 261 and the distal locking mechanism 262 (see e.g., FIG. 7). Accordingly, when the extension set 260 is coupled to the coupling surface 212, the longitudinal centerline C of the stabilization device 200 and the longitudinal axis A defined by the extension set 260 are aligned and/or substantially coaxial and the side port 263 of the extension set 260 can be placed in contact with, disposed in, and/or extend through the side channel 216 on a left side of the stabilization device 200 or on a right side of the stabilization device 200.

In some embodiments, the arrangement of the coupling surface 212 and the extension set 260 can be such that the extension set 260 is placed in contact with the coupling surface 212 and rotated into a position in which the side port 263 is disposed in one of the side channels 216. In some embodiments, a portion of the coupling surface 212 that forms and/or defines the side channels 212 can form a snap or press fit with at least a portion of the side port 263 of the extension set 260. Moreover, in use, the side port 263 of the extension set 260 is typically coupled to a flexible tubing 265 (see e.g., FIG. 7) or the like and, as such, the side channels 216 can be configured to allow the coupling of the flexible tubing 265 to the side port 263 of the extension set 260 without resulting in undue bending or kinking of the flexible tubing 265.

In some embodiments, the shape and/or contour of the coupling surface 212 can be configured to place and/or maintain a VAD (e.g., the IV catheter 250) at a predetermined, predefined, and/or otherwise desired angle relative to the skin of the patient at or near the insertion site of the IV catheter 250 (or target location). For example, in some embodiments, the coupling surface 212 can be angled such that a height of the coupling surface 212 at or near the proximal end portion 202 is greater than a height of the coupling surface 212 at or near the distal end portion 206. In some embodiments, the coupling surface 212 can be configured to receive, couple to, and/or secure the IV catheter 250 at an angle between, for example, about 3° and about 15° relative to the skin of the patient at the insertion site. Specifically, in some embodiments, the coupling surface 212 can be configured to receive, couple to, and/or secure the IV catheter 250 at an angle of about 10°, about 8°, about 6°, or less. In some embodiments, the coupling surface 212 of the stabilization device 200 can be arranged to secure the IV catheter 250 at any suitable angle based at least in part on an angle of insertion of, for example, the IV catheter. For example, in some embodiments, the coupling surface 212 can be configured to place and/or maintain the IV catheter 250 at an angle that can minimize a risk or likelihood of the IV catheter 250 becoming kinked (e.g., at the IV catheter insertion site or skin entry).

In some embodiments, the stabilization device 200 can be configured to secure the IV catheter 250 at an angle that is based at least in part on an IV insertion site. For example, in some embodiments, a stabilization device can be configured to secure an IV catheter at a first angle when the IV catheter is inserted into, for example, the antecubital fossa and a second angle, different from the first angle, when the IV catheter is inserted into, for example, the hand. In such embodiments, the stabilization device 200 can include an indicator and/or can have a color or the like configured provide an indication to a user associated with the intended use or intended insertion site.

Figure 8:
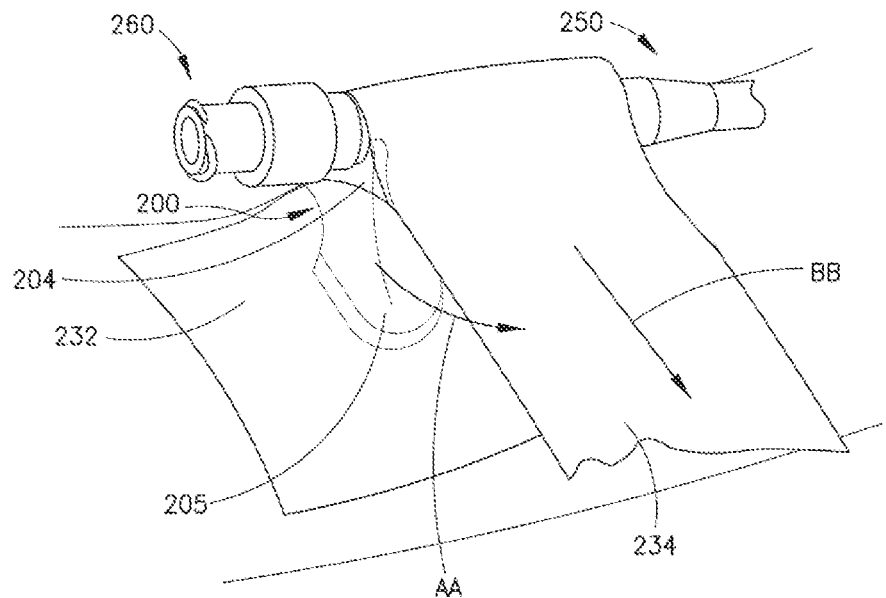
FIGS. 8 and 9 are a right-side perspective view and a top view, respectively, of the stabilization device and vascular access device of FIG. 7 secured to a target location of a patient.
Figure 9:
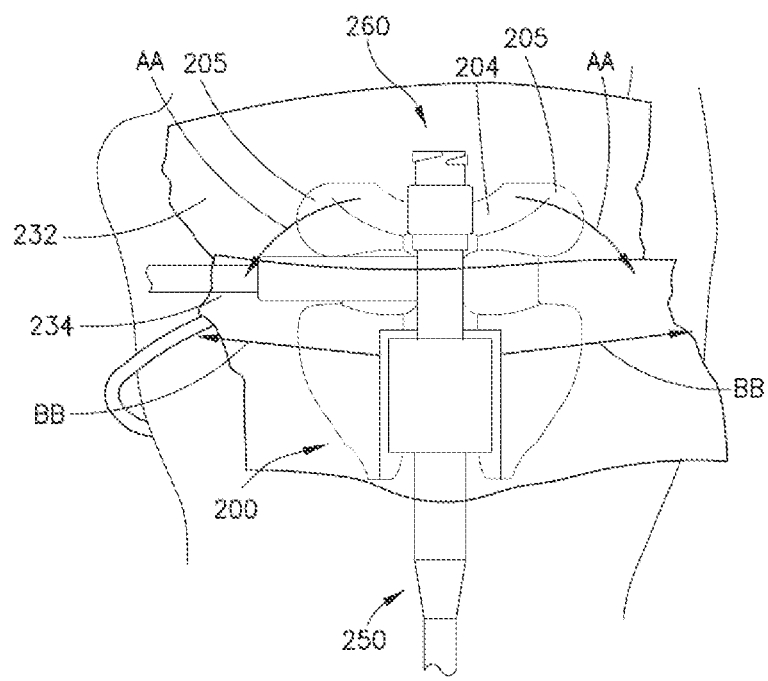
Figure 10:
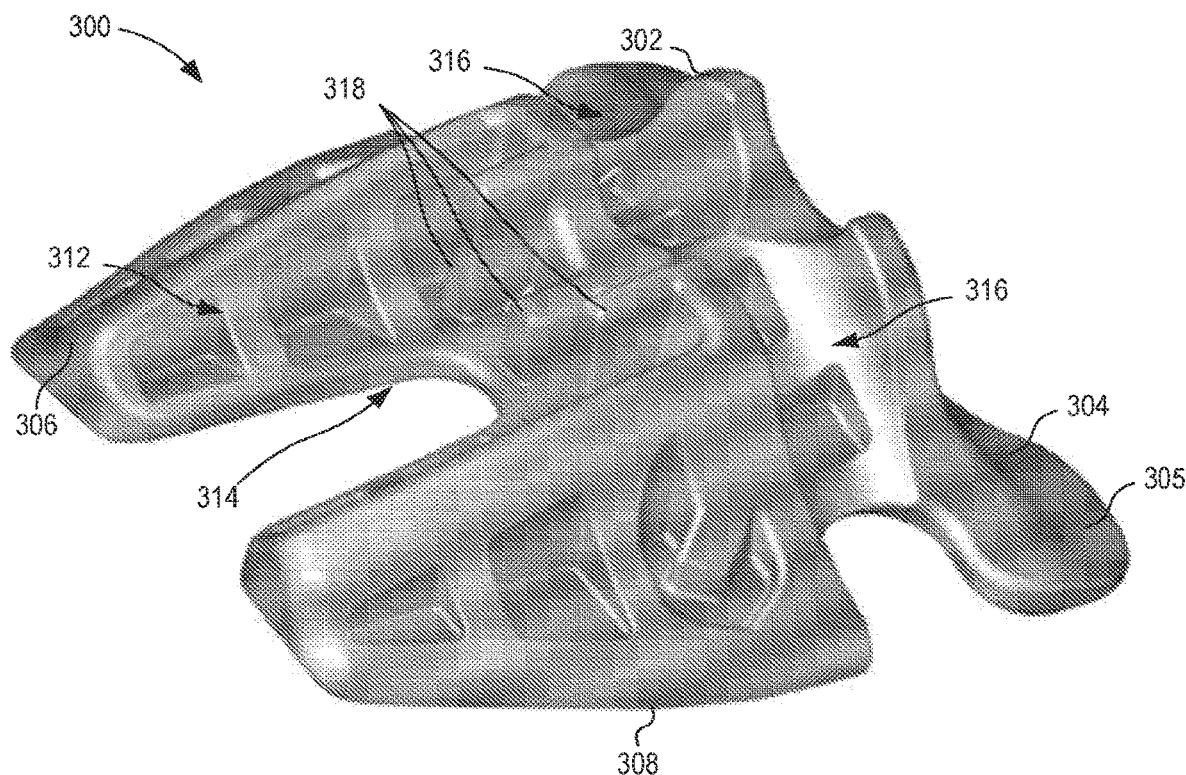
FIG. 10-13 are various views of a stabilization device according to an embodiment.
Figure 11:
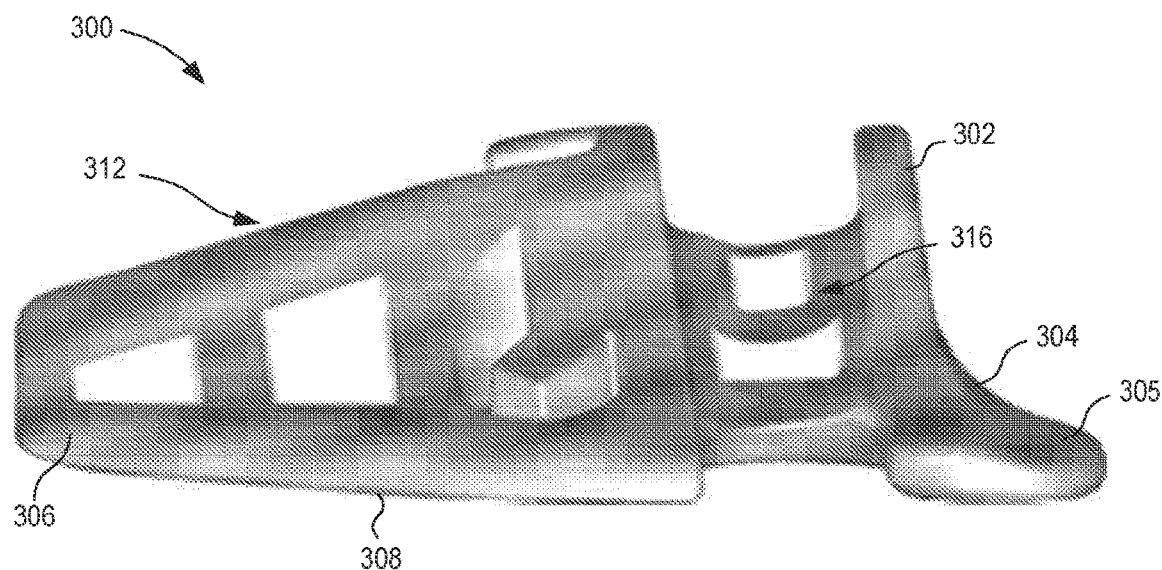

As shown in FIGS. 7-9, the stabilization device 200 is configured to secure and/or stabilize the IV catheter 250 relative to, for example, a target location of a patient. For example, in some instances, the IV catheter 250 can be inserted into the hand of a patient (e.g., at or along a target location) such that (1) a portion of the IV catheter 250 is disposed within a vein (insertion of the IV catheter 250 is not shown in FIGS. 7-9) and (2) a hub of the IV catheter 250 is disposed outside of the patient. In some instances, the extension set 260 (e.g., the T-adapter) can be physically and fluidically coupled to the hub of the IV catheter 250.

With the extension set 260 coupled to the IV hub, a user (e.g., a doctor, nurse, technician, physician, surgeon, and/or other medical professional) can manipulate the stabilization device 200 by placing a portion of the extension set 260 in contact with the coupling surface 212 of the stabilization device 200. As described above, the coupling surface 212 can be configured to form a friction fit and/or the like with the portion of the extension set 260 to couple the extension set 260 to the stabilization device 200. As shown, for example, in FIG. 7, the extension set 260 can be coupled to the coupling surface 212 of the stabilization device 200 such that the distal locking mechanism 262 or the like of the extension set 260 is at least partially disposed in and/or otherwise aligned with the distal notch 214. As described above, such an arrangement can allow the user to engage the distal locking mechanism 262 to couple the extension set 260 to or decouple the extension set 260 from the IV catheter 250. In addition, the side port 263 of the extension set 260 is positioned within one of the side channels 216 (see e.g., FIG. 7) such that the flexible tubing 265 coupled to the side port 263 can extend out of the side channel 216. Accordingly, the side port 263 of the extension set 260 can be used to deliver fluid to or withdraw fluid from the vein in which the IV catheter 250 is disposed. Furthermore, the proximal port or locking mechanism 261 of the extension set 260 can be disposed in a proximal position relative to the proximal surface 204 when the extension set 260 is coupled to the coupling surface 212. In this manner, any suitable device can couple to the proximal port or locking mechanism 261 to deliver fluids to, withdraw fluids from, and/or otherwise gain access to the vein in which the IV catheter 250 is disposed.

Once the stabilization device 200 is coupled to the extension set 260, the stabilization device 200 can be positioned on the skin of the patient (e.g., at or near the insertion site or target location). In this example, the IV catheter 250 is inserted into the hand of the patient and thus, the stabilization device 200 is positioned relative to the hand of the patient. Thus, the base surface 208 of the stabilization device 200 can be placed in contact with the skin of the patient at or near the insertion site of the IV catheter 250 and/or otherwise at or near a target location of the patient. As described above, the stabilization device 200 can be adjusted and/or positioned such that the recess 210 is aligned with and/or otherwise disposed about or over the vein in which the IV catheter 250 is disposed. In this manner, securing the stabilization device 200 to the skin of the patient does not result in the base surface 208 exerting a force on the vein that may otherwise be sufficient to occlude and/or restrict flow through the vein.

Having coupled the stabilization device 200 to the extension set 260 and having placed the stabilization device 200 in the desired position at or near the insertion site (e.g., such that the recess 210 is aligned with or disposed over the vein in which the IV catheter 250 is disposed), the user can secure the stabilization device 200 to the patient. In some embodiments, the user can secure the stabilization device 200 via medical tape or the like, as shown, for example, in FIGS. 8 and 9. More particularly, in some instances, a user can remove a first strip of medical tape 232 from a roll of medical tape and can apply the first strip of medical tape 232 to the proximal surface 204 of the stabilization device 200 such that a first portion of the medical tape is adhered to the proximal surface 204 and a second portion of the medical tape is adhered to the skin of the patient. For example, in some instances, the user can place the first strip of the medical tape 232 such that a first portion of the width of the first strip 232 overlays and/or is adhered to the proximal surface 204 of the stabilization device 200 while a second portion of the width of the first strip 232 overlays and/or is adhered to the skin of the patient, as shown in FIGS. 8 and 9.

As described above, the proximal surface 204 can have a shape, size, and/or configuration that facilitates the securement of the stabilization device 200. For example, in some embodiments, the proximal surface 204 can be angled and/or can have a relatively curved contour or the like such that when the user applies the first strip of medical tape 232 to the proximal surface 204, the tape curves bends, conforms, and/or otherwise forms a shape and/or follows a path that is at least partially based on the shape of the proximal surface 204. As shown in FIGS. 8 and 9, the shape and/or configuration of the proximal surface 204 is such that a portion of the first strip of medical tape overlays and/or is adhered to the extensions 205. Moreover, the arrangement of the proximal surface 204 and/or the extensions 205 is such that the first strip of medical tape 232 curves and/or bends such that end portions of the first strip 232 are adhered to the skin of the patient and positioned distal to, for example, a medial or middle portion of the first strip 232, as indicated by the arrows AA in FIGS. 8 and 9.

After securing the first strip of medical tape 232, the user can remove a second strip of medical tape 234 from the roll of medical tape and can apply the second strip of medical tape 234 transversely across a portion of the stabilization device 200 and the IV catheter 250, as indicated by the arrows BB in FIGS. 8 and 9. As shown, the user can apply the second strip of medical tape 234 such that a first end portion of the second strip of medical tape 234 is adhered to a portion of the patient's skin on a first side of the stabilization device 200; a second end portion of the second strip of medical tape 234 is adhered to a portion of the patient's skin on a second side of the stabilization device 200 substantially opposite the first side of the stabilization device 200; and a medial or middle portion (e.g., between the first end portion and the second end portion) is adhered to at least one of the stabilization device 200 or the IV catheter 250.

Moreover, the first end portion of the second strip of medical tape 234 can at least partially overlap a first end portion of the first strip of medical tape 232 and the second end portion of the second strip of medical tape 234 can at least partially overlap a second end portion of the first strip of medical tape 232, as shown in FIGS. 8 and 9. In some embodiments, positioning a portion of the second strip of medical tape 234 over a portion of the first strip of medical tape 232 can enhance the adhesion of at least one of the first strip 232 or the second strip 234. In other words, positioning a portion of the second strip of medical tape 234 over a portion of the first strip of medical tape 232 can reduce a likelihood of the portion of the first strip of medical tape 232 from working loose, decoupling, and/or otherwise breaking the adhesive bond.

As described above, securing the stabilization device 200 to the skin of the patient (e.g., via the strips of medical tape 232 and 234) results in the stabilization device 200 and/or the medical tape securing, stabilizing, and/or substantially immobilizing the IV catheter 250 relative to the patient. That is to say, the arrangement of the stabilization device 200 is such that securing the stabilization device 200 and the IV catheter 250 to the skin of the patient can reduce and/or substantially prevent movement of the IV catheter 250 or at least an IV catheter thereof relative to the vein in which the IV catheter is at least partially disposed, as described in further detail herein with respect to a specific embodiment. Moreover, the arrangement of the recess 210 along the base surface 208 is such that securing and/or adhering the stabilization device 200 to the skin of the patient does not exert a force on the vein in which the IV catheter 250 is disposed, thereby reducing and/or substantially eliminating any obstruction and/or restriction otherwise resulting from such a force.

While the stabilization device 200 is described above with reference to FIGS. 7-9 as being secured to the skin of a patient via, for example, two strips of medical tape, it should be understood that the stabilization device 200 can be secured to the skin of the patient in any suitable manner. For example, although not shown, in some embodiments, the stabilization device 200 can be secured to the skin via a transparent dressing or the like such as, for example, Tegaderm™ and/or the like. In such instances, the transparent dressing can include an adhesive or the like disposed around the perimeter of the dressing or along one or more edges of the dressing. In some embodiments, the transparent dressing can be sized and/or shaped for use with the stabilization device 200. For example, the transparent dressing can have a size or shape that allows the dressing to cover at least the IV insertion site while allowing access to, for example, a proximal port of the extension set 260 or the IV catheter 250 (e.g., similar to the medical tape shown in FIGS. 8 and 9). In some instances, multiple methods of securing the stabilization device 200 to the skin can be used such as, for example, a combination of transparent dressing and medical tape, and/or any other suitable method of securement (such as an adhesive or the like).

FIGS. 10-15 illustrate a stabilization device 300 according to an embodiment. As described above with reference to the stabilization devices 100 and/or 200, the stabilization device 300 is configured to be placed in contact with the skin of a patient at or near an insertion site of an indwelling or placed vascular access device (VAD). The stabilization device 300 is configured to couple to and/or otherwise engage the VAD and/or a device or adapter coupled to the VAD (e.g., an extension set). Once coupled to the VAD and/or the device or adapter coupled to the VAD, the stabilization device 300 can be secured to the skin of the patient, which in turn, secures and/or stabilizes at least a portion of the VAD relative to the patient, as described in further detail herein.

The stabilization device 300 can be any suitable shape, size, and/or configuration. For example, in some embodiments, the stabilization device 300 can have a size and/or shape that is based at least in part on a size and/or shape of the VAD to be stabilized. In some embodiments, the size and/or shape of the stabilization device 300 can facilitate ease of use, for example, by simplifying a process of securing the stabilization device 300 to the VAD, the device or adapter coupled to the VAD, and/or the skin of a patient. In some embodiments, the size and/or shape of the stabilization device 300 can increase ergonomics, grip, and/or the like. For example, in some embodiments, the stabilization device 300 and/or a portion thereof can allow a user maintain a secure grip on the stabilization device 300 as the user couples (or decouples) one or more devices to a VAD, an extension set, and/or any other suitable device being stabilized, as described above with reference to the stabilization device 200. In some embodiments, aspects and/or portions of the stabilization device 300 can be substantially similar to corresponding aspects and/or portions of the stabilization device 200. Accordingly, such aspects and/or portions of the stabilization device 300 are not described in further detail herein.

As shown in FIGS. 10-13, the stabilization device 300 has a proximal end portion 302 and a distal end portion 306, and has a base surface 308 and a coupling surface 312. In general, the coupling surface 312 is configured to receive, retain, and/or otherwise couple to an extension set 360 such as, for example, a T-adapter or T-connector, which in turn is coupled to an indwelling or placed VAD, as described above with reference to the coupling surface 212 of the stabilization device 200. In this embodiment, the indwelling or placed VAD can be, for example, an IV catheter 350 (see e.g., FIGS. 14 and 15). The base surface 308 is configured to be placed in contact with the skin of a patient in a predetermined and/or desired manner at or near an insertion site of the IV catheter 350 or the like (also referred to herein as a "target location"). Once the stabilization device 300 is coupled to the extension set 360 and the base surface 308 is in contact with the skin of the patient at or near the insertion site, the stabilization device 300 (and the extension set 360) can be secured to the skin of the patient to secure and/or stabilize at least a portion of the IV catheter 350 relative to the patient and/or the vein in which the IV catheter 350 is disposed, as described above with reference to the stabilization device 200.

The proximal end portion 302 has a proximal surface 304 that has a predetermined and/or desired shape. For example, the proximal surface 304 can be angled, tapered, flared, curved, rounded, and/or the like (see e.g., FIGS. 10-12). In some embodiments, the proximal surface 304 can have a rounded, curved, parabolic, and/or substantially bell-shaped perimeter (see e.g., FIG. 13). Moreover, the proximal end portion 302 and/or the proximal surface 304 can include a set of extensions 305 (e.g., feet, tabs, pads, protrusions, etc.) that extend transversely away from a center of the stabilization device 300. In some embodiments, the arrangement and/or shape of the proximal surface 304 and/or the extensions 305 can facilitate the coupling or securing of the stabilization device 300 to the skin of the patient (e.g., via medical tape or the like), as described in detail above with reference to the stabilization device 200.

Figure 12:
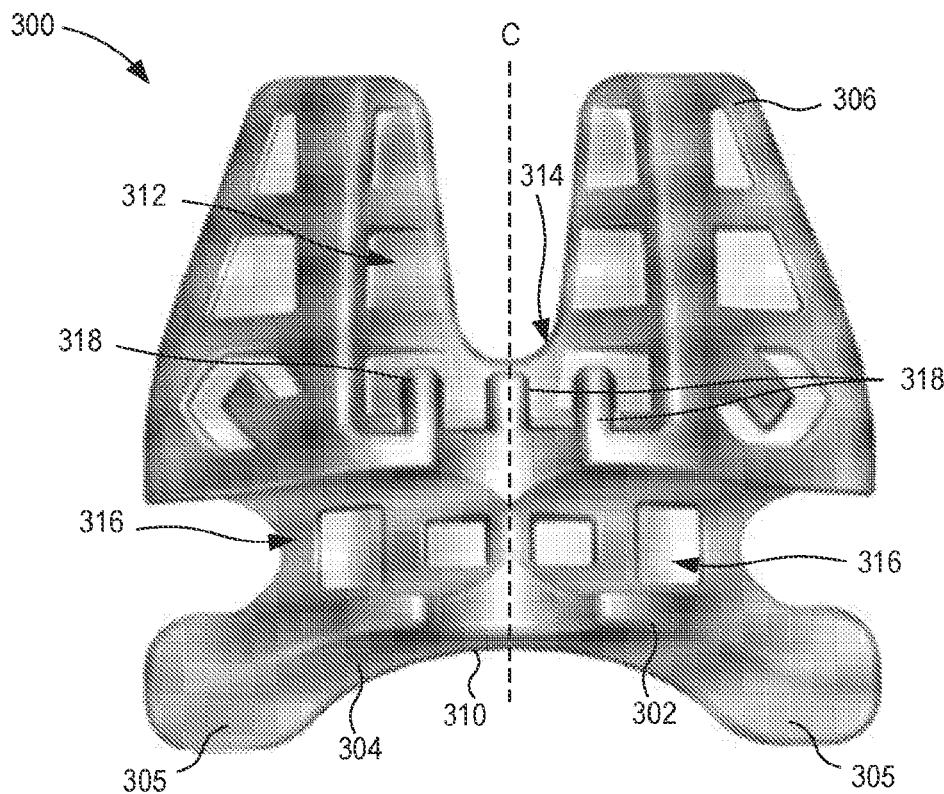
Figure 13:
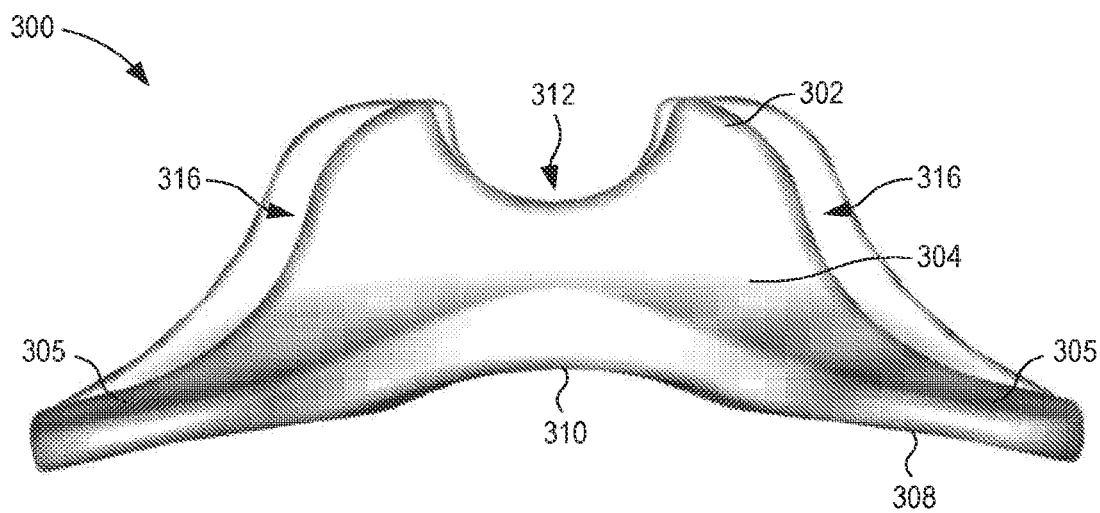

The base surface 308 can be any suitable shape and/or configuration. For example, as shown in FIGS. 12 and 13, the base surface 308 can have a contour and/or shape that is generally concave. In some embodiments, the concave contour and/or shape can be based at least in part on a curvature and/or shape of a portion of the patient's anatomy. For example, in some embodiments, the base surface 308 can have a contour and/or shape that is based at least in part on a general contour and/or curvature of a target location and/or IV insertion site of a patient. For example, as described above with reference to the base surface 208 of the stabilization device 200, in some embodiments, the contour and/or curvature can be based on a shape and/or curve of a patient's hand or forearm (or other suitable insertion site and/or target location).

As shown in FIG. 13, the base surface 308 defines a recess 310 (e.g., a notch, indentation, cutout, etc.) that extends along the base surface 308 in the direction of a longitudinal centerline of the stabilization device 300. In other words, the recess 310 extends along the base surface 308 in a proximal-distal direction. In some embodiments, the recess 310 extends along the base surface 308 through the proximal end portion 302 and through the distal end portion 306, as described above with reference to the stabilization devices 100 and/or 200. In some embodiments, the base surface 308 and the recess 310 can be similar to and/or substantially the same as the base surface 208 and the recess 210, respectively, of the stabilization device 200. Accordingly, the size, shape, configuration, and/or form of the base surface 308 and/or the recess 310 are not described in further detail herein.

As described above with reference to the stabilization device 200, the stabilization device 300 is configured to be placed in a position at or on a target location (e.g., along the skin of the patient at or near an IV insertion site) such that the recess 310 is aligned with and/or otherwise disposed over the vein in which the IV catheter 350 is disposed. In some embodiments, when the base surface 308 of the stabilization device 300 is placed in contact with the skin of the patient, the recess 310 can be spaced apart from the skin of the patient (e.g., not in contact with the skin of the patient). In some embodiments, the recess 310 can have a height (or depth) and a width that are each larger than a diameter of the vein in which the IV catheter 350 is to be disposed. In other words, a size and/or shape of the recess 310 can be based at least in part on a size and/or shape of a vein over which the stabilization device 300 is disposed. As such, the recess 310 can have a height and/or width that is sufficiently large to allow the recess 310 to be disposed over and/or above or about a vein that can vary in size, shape, and/or arrangement. Moreover, forming and/or defining the recess 310 to be larger (e.g., in height and/or width) than the vein in which the IV catheter 350 is disposed can, for example, reduce an amount of force that would otherwise be exerted by the base surface 308 on the vein and/or can allow for movement and/or reconfiguration of a portion of the patient while continuing to provide stabilization to or for the IV catheter 350, as described in detail above with reference to the stabilization device 200.

The coupling surface 312 of the stabilization device 300 can be any suitable shape, size, and/or configuration. In the embodiment shown in FIGS. 10-15, the coupling surface 312 can form a contour or shape that is at least partially based on a shape of the extension set 360. In some embodiments, the coupling surface 312 can be configured to contact and/or engage an outer surface of the extension set 360 to form and/or define a friction fit therebetween. That is to say, at least a portion of the coupling surface 312 can have a size and/or shape that is slightly undersized relative to a corresponding portion of the extension set 360 to form a friction fit, press fit, interference fit, etc. when the extension set 360 is in contact with the coupling surface 312.

In some embodiments, the coupling surface 312 can be configured to receive and/or couple to a T-shaped adapter or connector (e.g., the extension set 360), which in turn is coupled to a VAD (e.g., the IV catheter 350). As such, the stabilization device 300 can be configured to stabilize, support, and/or secure the VAD or IV catheter 350 when the coupling surface 312 is placed in contact with the T-shaped adapter, connector, and/or extension set 360. In some embodiments, the shape and/or contour of the coupling surface 312 can be configured to place and/or maintain a VAD (e.g., the IV catheter 350) at a predetermined, predefined, and/or otherwise desired angle relative to the skin of the patient at or near the insertion site of the IV catheter 350 (or target location). For example, in some embodiments, the coupling surface 312 can be angled such that a height of the coupling surface 312 at or near the proximal end portion 302 is greater than a height of the coupling surface 312 at or near the distal end portion 306. In some embodiments, the coupling surface 312 can be configured to receive, couple to, and/or secure the IV catheter 350 at an angle between, for example, about 3° and about 15° relative to the skin of the patient at or near the insertion site. In some embodiments, the coupling surface 312 of the stabilization device 300 can be arranged to secure the IV catheter 350 at any suitable angle based at least in part on an angle of insertion of, for example, the IV catheter 350 and/or the insertion site of the patient, as described in detail above with reference to the stabilization device 200.

As shown, for example, in FIG. 12, the coupling surface 312 includes a distal notch 314, one or more side channels 316, and one or more protrusions 318. The distal notch 314 formed by and/or along the coupling surface 312 can be configured to accommodate a distal locking mechanism 362 (e.g., a Luer Lok®) of the extension set 360. For example, in some embodiments, the extension set 360 (e.g., the T-adapter) can include a rotatable lock at a distal end portion thereof that is configured to physically and fluidically couple the extension set 360 to the IV catheter 350. Accordingly, the distal notch 314 can provide sufficient space for a user to grasp and rotate the rotatable lock to couple or decouple the distal locking mechanism 362 of the extension set 360 to or from the IV catheter 350, as described above with reference to the coupling surface 212 of the stabilizing device 200.

Figure 14:
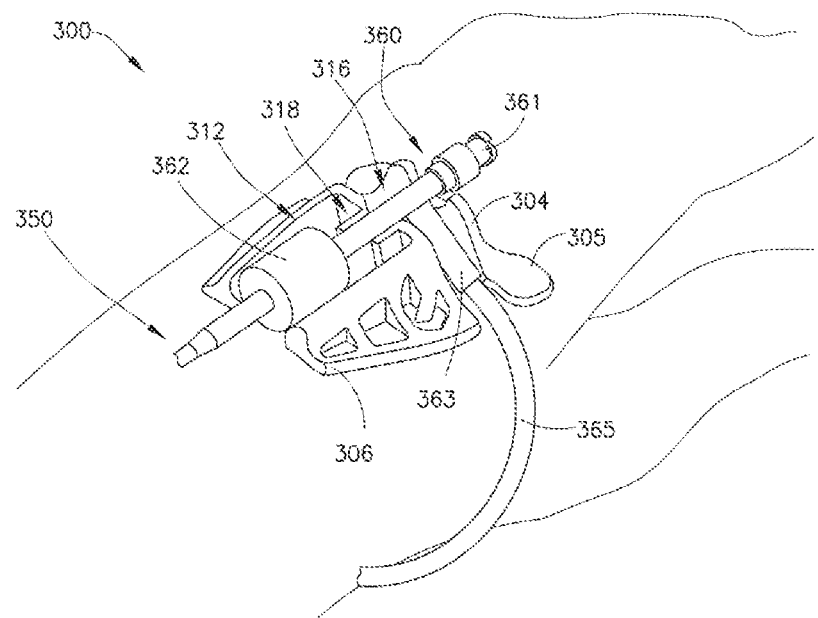
FIGS. 14 and 15 are a left-side perspective view and a top view, respectively, of the stabilization device of FIGS. 10-13 coupled to a vascular access device and positioned at a target location of a patient.
Figure 15:
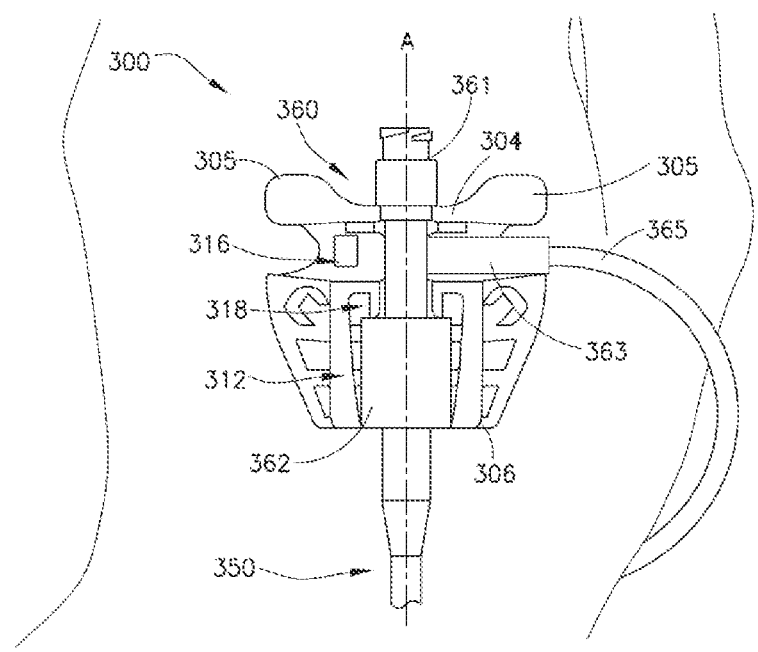

The one or more side channels 316 of the stabilization device 300 can be any suitable shape, size, and/or configuration. In the embodiment shown in FIGS. 10-15, the stabilization device 300 includes two side channels 316, with one side channel 316 on opposite sides of the stabilization device 300 and extending in a perpendicular and/or transverse direction relative to, for example, a longitudinal centerline C of the stabilization device 300 (see e.g., FIG. 12). At least one of the side channels 316 is configured to receive a side port 363 of the extension set 360. For example, as shown in FIGS. 14 and 15, the extension set 360 can be a dual port extension set having a "T" configuration in which the side port 363 is substantially perpendicular to a longitudinal axis A defined between the proximal locking mechanism 361 and the distal locking mechanism 362 (see e.g., FIG. 15). Accordingly, when the extension set 360 is coupled to the coupling surface 312, the longitudinal centerline C of the stabilization device 300 and the longitudinal axis A defined by the extension set 360 are aligned and/or substantially coaxial and the side port 363 of the extension set 360 can be placed in contact with, disposed in, and/or extend through the side channel 316 on a left side of the stabilization device 300 or on a right side of the stabilization device 300.

In some embodiments, the arrangement of the coupling surface 312 and the extension set 360 can be such that the extension set 360 is placed in contact with the coupling surface 312 and rotated into a position in which the side port 363 is disposed in one of the side channels 316. In some embodiments, a portion of the coupling surface 312 that forms and/or defines the side channels 312 can form a snap or press fit with at least a portion of the side port 363 of the extension set 360. Moreover, in use, the side port 363 of the extension set 360 is typically coupled to a flexible tubing 365 (see e.g., FIGS. 14 and 15) or the like and, as such, the side channels 316 can be configured to allow the coupling of the flexible tubing 365 to the side port 363 of the extension set 360 without resulting in undue bending or kinking of the flexible tubing 365.

In some embodiments, the one or more protrusions 318 of the coupling surface 312 can be arranged and/or configured to ensure the stabilization device 300 is in a desired orientation and/or is facing a desired direction when the coupling surface 312 is placed in contact with the extension set 360. For example, as shown in FIG. 12, the coupling surface 312 can include a set of protrusions 318 that extend from a portion of the coupling surface 312 that is distal to the side channels 316. The set of protrusions 318 can be any suitable configuration and/or arrangement. For example, while the coupling surface 312 is shown as including a set of three protrusions 318, in other embodiments, the coupling surface 312 can include any number of protrusions 318 (e.g., one protrusion, two protrusions, four protrusions, five protrusions, or more). In some embodiments, the protrusions 318 can be substantially uniform or can have one or more different heights, widths, lengths, etc.

In some embodiments, the protrusions 318 can be configured to selectively engage a portion of the extension set 360 such that the coupling surface 312 is placed in a desired position and/or orientation relative to the extension set 360. For example, in some embodiments, the arrangement of the protrusions 318 can be such that when the distal end portion 306 of the stabilization device 300 is aligned with or placed in contact with the distal locking mechanism 362, the side port 363 of the extension set 360 is aligned with the side channels 316. More specifically, when the coupling surface 312 is placed in contact with the extension set 360 such that a portion of the distal locking mechanism 362 is disposed in and/or aligned with the distal notch 314 defined by the coupling surface 312, the side port 363 of the extension set 360 is aligned with and capable of being disposed in one of the side channels 316, as shown in FIGS. 14 and 15. In other words, when the distal end portion 306 of the stabilization device 300 and the distal locking mechanism 362 are placed in the same orientation (e.g., when the stabilization device 300 and the extension set 360 are facing the same direction), the side port 363 of the extension set 360 can be positioned in one of the side channels 316. Said yet another way, when the distal locking mechanism 362 is disposed in and/or aligned with the distal notch 314 defined by the coupling surface 312, a position of the side port 363 along the longitudinal axis A of the extension set 360 is substantially aligned with a position of the side channels 316 along the longitudinal centerline C of the stabilization device 300, thereby allowing the side port 363 to be disposed in one of the side channels 316.

As described above, the arrangement of the protrusions 318 can allow and/or can be configured to allow the coupling surface 312 to be placed in contact with and/or coupled to the extension set 360 when the stabilization device 300 is in a desired orientation relative to the extension set. Conversely, the arrangement of the protrusions 318 can be such that if the stabilization device 300 is placed in an undesired orientation relative to the extension set 360, the contact between the coupling surface 312 and the extension set 360 can be limited and/or a coupling therebetween can be limited and/or prevented. For example, in instances in which the distal end portion 306 of the stabilization device 300 and the distal locking mechanism 362 are not aligned the protrusions 318 can selectively engage a portion of the extension set 360, which in turn, results in the side port 363 of the extension set 360 being misaligned relative to the side channels 316.

In some embodiments, the misalignment between the side port 363 and the side channels 316 can limit and/or substantially prevent the coupling surface 312 from being placed in contact with and/or being coupled to the extension set 360, which can provide an indication to a user that the stabilization device 300 is in an undesirable orientation relative to the extension set 360 (and/or vice versa). For example, in some instances, the protrusions 318 can selectively engage a portion of the extension set 360 to misalign the side port 363 relative to the side channels 316 when the stabilization device 300 and the extension set 360 are placed in opposite directions and/or orientations. More particularly, the protrusions 318 can selectively engage a portion of the extension set 360 to misalign the side port 363 relative to the side channels 316 when the coupling surface 312 of the stabilization device 300 is at least partially placed in contact with the extension set 360 such that the proximal locking mechanism 361 of the extension set 360 is aligned with and/or at least partially disposed in the distal notch 314 defined by the coupling surface 312. Said another way, when the proximal locking mechanism 361 of the extension set 360 is disposed in and/or aligned with the distal notch 314 defined by the coupling surface 312, a position of the side port 363 along the longitudinal axis A of the extension set 360 is misaligned relative to a position of the side channels 316 along the longitudinal centerline C of the stabilization device 300, which, in turn, can limit and/or substantially prevent the side port 363 from being disposed in one of the side channels 316. Put simply, in some embodiments, the protrusions 318 can limit and/or substantially prevent the stabilization device 300 from being placed in a desired contact with or coupled to the extension set 360 while the stabilization device 300 is in a backwards orientation relative to the extension set 360.

As described above with reference to the stabilization device 200, the stabilization device 300 is configured to secure and/or stabilize the IV catheter 350 relative to, for example, a target location of a patient. For example, in some instances, the IV catheter 350 can be inserted into the hand of a patient (e.g., at or along a target location) such that (1) a portion of the IV catheter 350 is disposed within a vein and (2) a hub of the IV catheter 350 is disposed outside of the patient. In some instances, the extension set 360 (e.g., the T-adapter) can be physically and fluidically coupled to the hub of the IV catheter 350.

With the extension set 360 coupled to the IV hub, a user (e.g., a doctor, nurse, technician, physician, surgeon, and/or other medical professional) can manipulate the stabilization device 300 by placing a portion of the extension set 360 in contact with the coupling surface 312 of the stabilization device 300. As described above, the coupling surface 312 can be configured to form a friction fit and/or the like with the portion of the extension set 360 to couple the extension set 360 to the stabilization device 300. Moreover, the arrangement of the protrusions 318 can be configured to selectively engage the extension set 360 such that a user can visually inspect whether the stabilization device 300 and the extension set 360 are placed in a desired orientation relative each other, as described in detail above. Accordingly, the stabilization device 300 can be placed in contact with and/or coupled to the extension set 360 as described in detail above and shown in, for example, FIGS. 14 and 15.

Once the stabilization device 300 is coupled to the extension set 360, the stabilization device 300 can be positioned on the skin of the patient (e.g., at or near the insertion site or target location). In this example, the IV catheter 350 is inserted into the hand of the patient and thus, the stabilization device 300 is positioned relative to the hand of the patient. Thus, the base surface 308 of the stabilization device 300 can be placed in contact with the skin of the patient at or near the insertion site of the IV catheter 350 and/or otherwise at or near a target location of the patient. As described above, the stabilization device 300 can be adjusted and/or positioned such that the recess 310 is aligned with and/or otherwise disposed about or over the vein in which the IV catheter 350 is disposed. In this manner, securing the stabilization device 300 to the skin of the patient does not result in the base surface 308 exerting a force on the vein that may otherwise be sufficient to occlude and/or restrict flow through the vein.

Having coupled the stabilization device 300 to the extension set 360 and having placed the stabilization device 300 in the desired position at or near the insertion site (e.g., such that the recess 310 is aligned with or disposed over the vein in which the IV catheter 350 is disposed), the user can secure the stabilization device 300 to the patient. For example, although not shown in FIGS. 14 and 15, in some instances, the user can secure the stabilization device 300 to the target location of the patient via medical tape or the like. More particularly, in some instances, a user can secure the stabilization device 300 to the target location of the patient using two strips of medical tape as described in detail above with reference to the stabilization device 200 and FIGS. 8 and 9. While the stabilization device 300 is described as being secured to the target location of the patient via, for example, two strips of medical tape, it should be understood that the stabilization device 300 can be secured to the target location of the patient (e.g., skin of the patient at or near an IV insertion site) in any suitable manner such as those described above with reference to the stabilization device 200. Accordingly, the process of securing the stabilization device 300 to the target location of the patient is not described in further detail herein.

As described above, securing the stabilization device 300 to the skin of the patient (e.g., via the strips of medical tape 332 and 334) results in the stabilization device 300 and/or the medical tape securing, stabilizing, and/or substantially immobilizing the IV catheter 350 relative to the patient. That is to say, the arrangement of the stabilization device 300 is such that securing the stabilization device 300 and the IV catheter 350 to the skin of the patient can reduce and/or substantially prevent movement of the IV catheter 350 or at least an IV catheter thereof relative to the vein in which the IV catheter is at least partially disposed, as described in further detail herein with respect to a specific embodiment. Moreover, the arrangement of the recess 310 along the base surface 308 is such that securing and/or adhering the stabilization device 300 to the skin of the patient does not exert a force on the vein in which the IV catheter 350 is disposed, thereby reducing and/or substantially eliminating any obstruction and/or restriction otherwise resulting from such a force.

Figure 16:
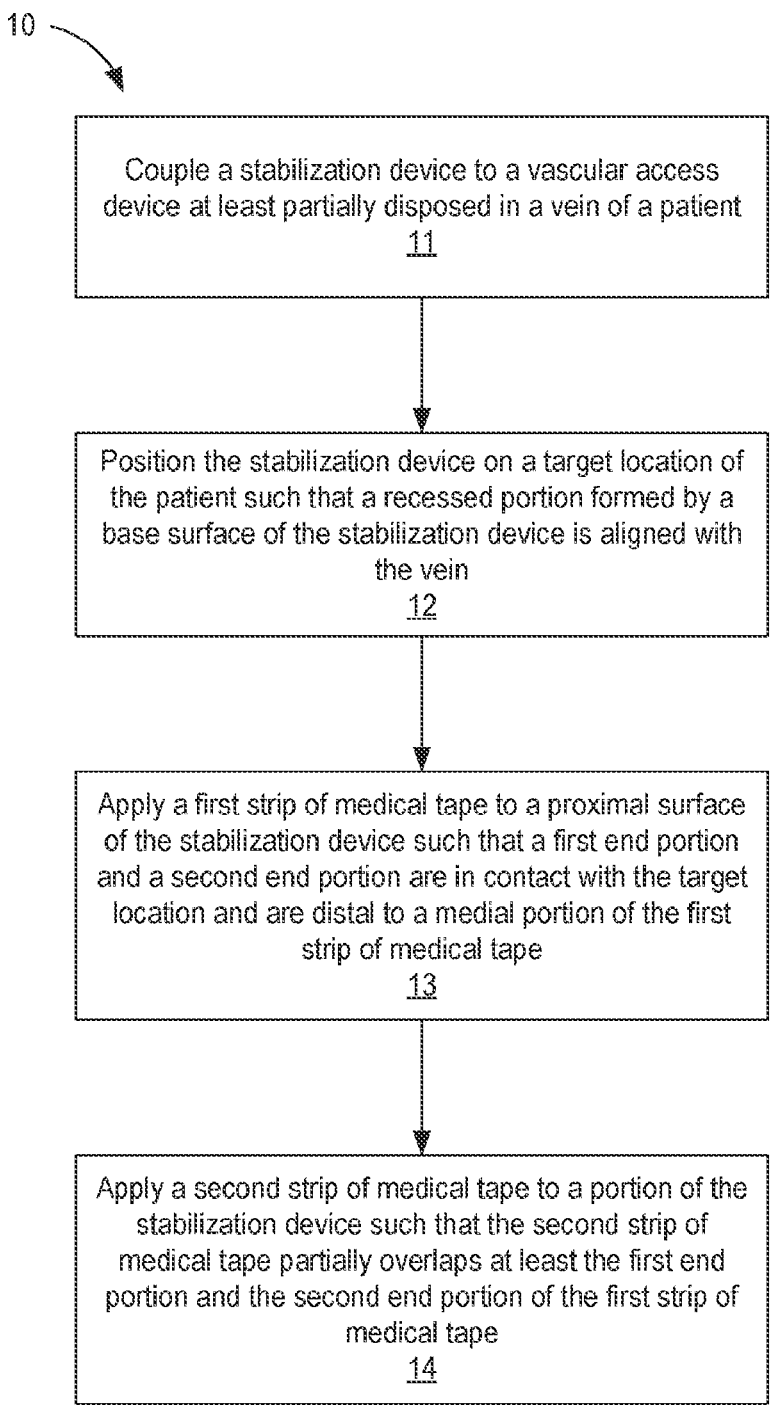
FIG. 16 is a flowchart illustrating a method of using a stabilization device according to an embodiment.

FIG. 16 is a flowchart illustrating a method 10 of using a stabilization device according to an embodiment. The stabilization device can be any suitable shape, size, and/or configuration. For example, in some embodiments, the stabilization device can be substantially similar to the stabilization devices 100, 200, and/or 300 described above. Accordingly, the stabilization device can be used to secure and/or stabilize a vascular access device (VAD) at least partially disposed in a patient. As described above, the VAD can be any suitable device or set of devices. For example, in some embodiments, the VAD can be an IV catheter. In other embodiments, the VAD can be an adapter or connector (e.g., an extension set) coupled to an indwelling or placed IV catheter.

As shown in FIG. 16, the method 10 includes coupling the stabilization device to the VAD at least partially disposed in a vein of a patient, at 11. As described above with reference to the stabilization devices 200 and/or 300, the stabilization device can include a coupling surface (e.g., the coupling surfaces 212 and/or 312) configured to receive and/or couple to a portion of the VAD. For example, in some embodiments, the VAD can include and/or can be an IV catheter that is coupled to an IV extension set or the like. As described above with reference to the stabilization devices 200 and/or 300, the extensions set can be a dual port extension set or adapter having, for example, a T-configuration or the like. In such embodiments, the coupling of the stabilization device to the VAD can include placing the extension set in contact with the coupling surface of the stabilization device such that a side port or the like of the extension set is aligned with and/or in contact with a side channel included in and/or formed by the coupling surface (see e.g., FIGS. 7, 14, and/or 15).

In some embodiments, the coupling surface can include one or more features, protrusions, members, etc. configured to selectively engage a portion of the VAD or adapter if, for example, the stabilization device, VAD, and/or adapter are in an undesirable orientation or the like, as described above with reference to the coupling surface 312. For example, in some embodiments, the coupling of the stabilization device to the VAD includes coupling the stabilization device to an extension set, aligning a longitudinal axis of the extension set with a longitudinal centerline of the stabilization device (e.g., such that the longitudinal axis and the longitudinal centerline are co-axial, parallel, and/or otherwise extending in a substantially similar direction), and placing the extension set in contact with the coupling surface of the stabilization device. As described above, when the stabilization device and/or the extension set are in a desired orientation and/or are otherwise facing in the same direction, the side port of the extension set can be aligned with and placed in contact with a side channel of the coupling surface. If, however, the stabilization and/or the extension set are not in a desired orientation and/or are otherwise facing in opposite directions, the features, protrusions, members, etc. of the coupling surface can engage a portion of the extension set, which in turn, can result in the side port of the extension set being misaligned relative to the side channel and thereby, substantially prevented from being placed in contact therewith (as described in detail above with reference to the stabilization device 300). In other embodiments, the coupling surface of the stabilization device need not include such a feature or the like.

After coupling the stabilization device to the VAD, the stabilization device is positioned on the skin of the patient (e.g., at a target location) such that a recessed portion formed by a base surface of the stabilization device is aligned with the vein, at 12. As described above with reference to the stabilization devices 100, 200, and/or 300, the recessed portion can be configured to reduce and/or substantially prevent the base surface from exerting an undesired force on the vein of the patient when the stabilization device is secured to the skin of the patient. Accordingly, the position of the stabilization device relative to the target location and/or an IV insertion site can be adjusted until the recessed portion is aligned with and/or disposed above or about the vein.

With the stabilization device in the desired position, a first strip of medical tape is applied to a proximal surface of the stabilization device such that each of a first end portion and a second end portion of the first strip of medical tape are in contact with the target location of the patient and are distal to a medial portion of the first strip of medical tape, at 13. As described above with reference to the stabilization device 200, the first strip of medical tape can be applied to the stabilization device such that a portion of the first strip overlays and/or is adhered to at least a portion of the proximal surface of the stabilization device. In some embodiments, the proximal surface of the stabilization device can have a size and/or shape that is configured to result in a bending or bowing of the first strip of medical tape when it is applied to the proximal surface (e.g., as described above with reference to FIGS. 8 and 9). The bending and/or bowing of the first strip of medical tape, in turn, results in each of the first end portion and the second end portion of the medical tape being secured to the target location of the patient (e.g., to the skin of the patient at or near the IV insertion site) in a distal position relative to the proximal surface of the stabilization device. Moreover, the medial portion of the first strip of medical tape (e.g., a middle portion) is at least partially in contact with the proximal surface of the stabilization device and at least partially in contact with the skin of the patient at or near the target location (see e.g., FIGS. 8 and 9).

The method 10 includes applying a second strip of medical tape to a portion of the stabilization device such that the second strip of medical tape partially overlaps at least the first end portion and the second end portion of the first strip of medical tape, at 14. For example, as described above with reference to FIGS. 8 and 9, the second strip of medical tape can be applied transversely to the portion of the stabilization device such that a first end portion of the second strip of medical tape is adhered to the skin of the patient and at least partially overlaps the first end portion of the first strip of medical tape; a second end portion of the second strip of medical tape is adhered to the skin of the patient and at least partially overlaps the second end portion of the first strip of medical tape; and a medial or middle portion of the second strip of medical tape is adhered to the portion of the stabilization device and/or to the extension set. Moreover, the portion of the stabilization device is distal to the proximal surface to which the first strip of medical tape is adhered. In some embodiments, positioning a portion of the second strip of medical tape over a portion of the first strip of medical tape can enhance the adhesion of at least one of the first strip or the second strip. In other words, positioning a portion of the second strip of medical tape over a portion of the first strip of medical tape can reduce a likelihood of the portion of the first strip of medical tape from working loose, decoupling, and/or otherwise breaking the adhesive bond.

In some embodiments, the arrangement of the first strip of medical tape and the second strip of medical tape can be such that a proximal locking mechanism of the extension set extends between and/or through a space, gap, and/or separation defined between, for example, the medial portion of the first strip of medical tape and the medial portion of the second strip of medical tape (see e.g., FIGS. 8 and 9). In other words, neither the first strip nor the second strip of medical tape obstructs the proximal locking mechanism of the extension set. Accordingly, any suitable device or the like can be coupled to the proximal locking mechanism of the extension set when the stabilization device is secured to the target location of the patient.

As described above, securing the stabilization device to the skin of the patient at, on, or near the target location (e.g., via the strips of medical tape) results in the stabilization device securing, stabilizing, and/or substantially immobilizing the IV catheter relative to the target location of the patient. That is to say, the arrangement of the stabilization device is such that securing the stabilization device and the IV catheter to the skin of the patient can reduce and/or substantially prevent movement of the IV catheter or at least an IV catheter thereof relative to the vein in which the IV catheter is at least partially disposed, as described in further detail herein with respect to a specific embodiment. Moreover, the arrangement of the recessed portion along the base surface is such that securing and/or adhering the stabilization device to the skin of the patient does not exert a force on the vein in which the IV catheter is disposed, thereby reducing and/or substantially eliminating any obstruction and/or restriction otherwise resulting from such a force.

While various embodiments have been described above, it should be understood that they have been presented by way of example only, and not limitation. Where schematics and/or embodiments described above indicate certain components arranged in certain orientations or positions, the arrangement of components may be modified. Although various embodiments have been described as having particular features and/or combinations of components, other embodiments are possible having a combination of any features and/or components from any of embodiments as discussed above. While the embodiments have been particularly shown and described, it will be understood that various changes in form and details may be made.

In some embodiments, the specific configurations of the various components can also be varied. For example, the size and specific shape of the various components can be different from the embodiments shown, while still providing the functions as described herein. More specifically, the size and shape of the various components can be specifically selected for a desired rate and/or volume of bodily fluid flow into a fluid reservoir. Likewise, the size and/or shape of the various components can be specifically selected for a desired or intended usage.

Where methods and/or schematics described above indicate certain events and/or flow patterns occurring in certain order, the ordering of certain events and/or flow patterns may be modified. Additionally certain events may be performed concurrently in parallel processes when possible, as well as performed sequentially.

What is claimed:

1. A method of stabilizing a vascular access device at least partially disposed within a vein of a patient, the method comprising:
   coupling a stabilization device to the vascular access device at least partially disposed in the vein of the patient, the stabilization device comprising:
      a coupling surface configured to be placed in contact with an adapter coupled to a proximal end portion of the access device,
      a proximal surface forming at least one angle configured to facilitate securement of the stabilization device to the target location of the patient, and
      a base surface forming a contoured portion and a recessed portion, the contoured portion configured to be placed in contact with the target location of the patient, the recessed portion configured to be spaced apart from the target location of the patient when the contoured portion is in contact with the target location of the patient;
   positioning the stabilization device on a target location of the patient such that the recessed portion is aligned with the vein;
   applying a first strip of medical tape to the proximal surface of the stabilization device such that each of a first end portion and a second end portion of the first strip of medical tape are in contact with the target location of the patient and are distal to a medial portion of the first strip of medical tape, the medial portion being at least partially in contact with the proximal surface of the stabilization device and at least partially in contact with the target location of the patient; and
   applying a second strip of medical tape to a portion of the stabilization device such that the second strip of medical tape partially overlaps at least the first end portion and the second end portion of the first strip of medical tape, the portion of the stabilization device being distal to the proximal surface.

2. The method of claim 1, wherein the vascular access device includes an intravenous catheter at least partially disposed in the vein of the patient, the coupling of the stabilization device to the vascular access device includes placing the coupling surface of the stabilization device in contact with an extension set coupled to a proximal hub of the intravenous catheter.

3. The method of claim 2, wherein the extension set has a proximal locking mechanism, a distal locking mechanism, and a side port, the extension set defines a longitudinal axis extending through the proximal locking mechanism and the distal locking mechanism, the side port is substantially perpendicular to the longitudinal axis.

4. The method of claim 3, wherein the coupling surface of the stabilization device includes a side channel that extends perpendicular to a longitudinal centerline of the stabilization device, the coupling of the stabilization device to the vascular access device includes coupling the stabilization device to the extension set such that (1) the longitudinal centerline of the stabilization device is aligned with the longitudinal axis of the extension set and (2) the side port of the extension set is placed in contact with the side channel of the stabilization device.

5. The method of claim 1, wherein the base surface includes a contoured portion and the recessed portion, the positioning of the stabilization device on the target location being such that the contoured portion of the base surface is in contact with the target location of the patient and the recessed portion of the base surface is spaced apart from the target location of the patient.

6. The method of claim 1, wherein applying the first strip of medical tape to the proximal surface of the stabilization device and applying the second strip of medical tape to the portion of the stabilization device is operable to secure the stabilization device to the target location of the patient, the stabilization device configured to stabilize the vascular access device when the stabilization device is secured to the target location.

7. The method of claim 6, wherein the stabilization device is configured to be secured to the target location of the patient such that (1) the contoured portion of the base surface is in contact with and exerts a force on the target location of the patient and (2) the recessed portion of the base surface is spaced apart from and does not exert a force on the target location of the patient.

\* \* \* \* \*